United States Patent
Campbell et al.

(10) Patent No.: US 11,207,294 B2
(45) Date of Patent: Dec. 28, 2021

(54) METHODS OF TREATING GENERALIZED PUSTULAR PSORIASIS WITH AN ANTAGONIST OF CCR6 OR CXCR2

(71) Applicant: CHEMOCENTRYX, INC., Mountain View, CA (US)

(72) Inventors: James J. Campbell, San Jose, CA (US); Karen Ebsworth, San Francisco, CA (US); Antoni Krasinski, Sunnyvale, CA (US); Venkat Reddy Mali, Cupertino, CA (US); Jeffrey McMahon, San Francisco, CA (US); Rajinder Singh, Belmont, CA (US); Ju Yang, Palo Alto, CA (US); Chao Yu, Sunnyvale, CA (US); Penglie Zhang, Foster City, CA (US)

(73) Assignee: ChemoCentryx, Inc., San Carlos, CA (US)

(*) Notice: Subject to any disclaimer, the term of this patent is extended or adjusted under 35 U.S.C. 154(b) by 0 days.

(21) Appl. No.: 16/241,469

(22) Filed: Jan. 7, 2019

(65) Prior Publication Data
US 2019/0209527 A1     Jul. 11, 2019

Related U.S. Application Data

(60) Provisional application No. 62/614,927, filed on Jan. 8, 2018, provisional application No. 62/715,503, filed on Aug. 7, 2018.

(51) Int. Cl.
| | | |
|---|---|---|
| *A61K 31/4035* | (2006.01) | |
| *A61P 17/06* | (2006.01) | |
| *A61P 29/00* | (2006.01) | |

(52) U.S. Cl.
CPC .......... *A61K 31/4035* (2013.01); *A61P 17/06* (2018.01); *A61P 29/00* (2018.01)

(58) Field of Classification Search
CPC ....... A61K 31/4035; A61P 17/06; A61P 29/00
See application file for complete search history.

(56) References Cited

U.S. PATENT DOCUMENTS

| | | | |
|---|---|---|---|
| 6,166,050 | A | 12/2000 | Lombardo et al. |
| 9,809,581 | B2 | 11/2017 | Chen et al. |
| 9,834,545 | B2 * | 12/2017 | Chen .................... C07D 405/12 |
| 10,336,736 | B2 | 7/2019 | Chen et al. |
| 10,370,363 | B2 | 8/2019 | Chen et al. |
| 2003/0204085 | A1 | 10/2003 | Taveras et al. |
| 2004/0097547 | A1 | 5/2004 | Taveras et al. |
| 2004/0106794 | A1 | 6/2004 | Taveras et al. |
| 2004/0147559 | A1 | 7/2004 | Taveras et al. |
| 2004/0209946 | A1 | 10/2004 | Yin et al. |
| 2008/0234266 | A1 | 9/2008 | Mederski et al. |
| 2008/0261917 | A1 | 10/2008 | Willems et al. |
| 2009/0306079 | A1 | 12/2009 | Taveras et al. |
| 2010/0029670 | A1 | 2/2010 | Baettig et al. |
| 2010/0267712 | A1 | 10/2010 | Heemskerk et al. |
| 2011/0086842 | A1 | 4/2011 | Stadtmueller et al. |
| 2011/0213029 | A1 | 9/2011 | Taveras et al. |
| 2013/0231393 | A1 | 9/2013 | Aubert |
| 2014/0296254 | A1 | 10/2014 | Musicki et al. |
| 2014/0309208 | A1 | 10/2014 | Musicki et al. |
| 2015/0087675 | A1 | 3/2015 | Musicki et al. |
| 2018/0141934 | A1 | 5/2018 | Chen et al. |

(Continued)

FOREIGN PATENT DOCUMENTS

| | | |
|---|---|---|
| WO | 01/64208 A1 | 9/2001 |
| WO | 01/92202 A1 | 12/2001 |

(Continued)

OTHER PUBLICATIONS

Wolf et al. IL-36R antibodies, potentially useful for the treatment of psoriasis: a patent evluation of WO2013074569. Expert Opin. Ther. Patents, 2014, 24(4): 477-479.*
Augey et al. Generalized pustular psoriasis (Zumbusch): a French epidemiological survey. Eur. J. Dermatol. 2006; 16(6): 669-73.*
Iizuka et al. Pathophysiology of generalized pustular psoriasis. Arch. Dermatol. Res. 2003, 295: S55-S59.*
Ozawa et al. Treatments of Generalized Pustular Psoriasis: A multicenter study in Japan. The Journal of Dermatology, vol. 26, 141-149, 1999.*
Solari et al. "Chemokine receptors as therapeutic agents: Why aren't there more drugs?" European Journal of Pharmacology, 746, 2015, 363-367.*
Mirza HA, Badri T, Kwan E. Generalized Pustular Psoriasis. [Updated Sep. 15, 2020], In: StatPearls [Internet]. Treasure Island (FL): StatPearls Publishing; Jan. 2021.*

(Continued)

*Primary Examiner* — Jared Barsky
(74) *Attorney, Agent, or Firm* — Mintz Levin Cohn Ferris Glovsky and Popeo PC

(57) ABSTRACT

The present disclosure provides, inter alia, methods of treating generalized pustular psoriasis (GPP) by administering an effective amount of a Chemokine Receptor 6 (CCR6) antagonist and/or a C—X—C motif chemokine receptor 2 (CXCR2) antagonist. Also provided herein are methods of modulating dysregulated IL-36 signaling in a subject in need thereof and methods of reducing neutrophil, inflammatory dendritic cell (iDC), and/or CD4 T cell accumulation in a subject in need thereof, said methods, include administering an effective amount of a Chemokine Receptor 6 (CCR6) antagonist and/or a C—X—C motif chemokine receptor 2 (CXCR2) antagonist. In some embodiments, the CCR6 and/or CXCR2 antagonist has the formula:

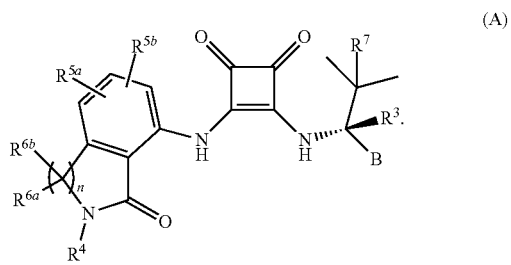

(A)

6 Claims, 46 Drawing Sheets

(56) References Cited

U.S. PATENT DOCUMENTS

| | | | |
|---|---|---|---|
| 2018/0170916 A1 | 6/2018 | Chen et al. | |
| 2020/0039969 A1 | 2/2020 | Chen et al. | |
| 2020/0140418 A1 | 5/2020 | Chen et al. | |

FOREIGN PATENT DOCUMENTS

| | | |
|---|---|---|
| WO | 02/057230 A1 | 7/2002 |
| WO | 02/067919 A1 | 9/2002 |
| WO | 02/076926 A1 | 10/2002 |
| WO | 02/083624 A1 | 10/2002 |
| WO | 03/080053 A1 | 10/2003 |
| WO | 2004/011418 A1 | 2/2004 |
| WO | 2005/075447 A1 | 8/2005 |
| WO | 2006/021544 A1 | 3/2006 |
| WO | 2007/014608 A1 | 2/2007 |
| WO | 2008/005570 A1 | 1/2008 |
| WO | 2008/109178 A1 | 9/2008 |
| WO | 2008/109179 A1 | 9/2008 |
| WO | 2008/148790 A1 | 12/2008 |
| WO | 2009/005801 A1 | 1/2009 |
| WO | 2009/005802 A1 | 1/2009 |
| WO | 2009/012375 A2 | 1/2009 |
| WO | 2009/073683 A2 | 6/2009 |
| WO | 2009/156421 A1 | 12/2009 |
| WO | 2010/045303 A2 | 4/2010 |
| WO | 2010/063802 A1 | 6/2010 |
| WO | 2010/091543 A1 | 8/2010 |
| WO | 2010/131145 A1 | 11/2010 |
| WO | 2010/131147 A1 | 11/2010 |
| WO | 2012/001076 A1 | 1/2012 |
| WO | 2012/080456 A1 | 6/2012 |
| WO | 2012/080457 A1 | 6/2012 |
| WO | 2013/030803 A1 | 3/2013 |
| WO | 2013/061002 A1 | 5/2013 |
| WO | 2013/061004 A1 | 5/2013 |
| WO | 2013/061005 A1 | 5/2013 |
| WO | 2013/174947 A1 | 11/2013 |
| WO | 2016/079049 A1 | 5/2016 |
| WO | 2017/087610 A1 | 5/2017 |

OTHER PUBLICATIONS

International Search Report and Written Opinion corresponding to PCT Application No. PCT/US2019/012519 dated Apr. 18, 2019; 13 pages.

European Search Report corresponding to EP 16867099.0 dated Feb. 20, 2019.

International Search Report and Written Opinion corresponding to PCT Application No. PCT/US2016/062417 dated Jan. 12, 2017, 12 pages.

International Search Report and Written Opinion corresponding to PCT Application No. PCT/US2016/062427 dated Feb. 21, 2017; 9 pages.

Aki, Cynthia et al., "Diaminocyclobutenediones as potent and orally available CXCR2 receptor antagonists: SAR in the phenolic amide region," *Bioorganic & Medicinal Chemistry Letters* (available online May 18, 2009); 19:4446-4449.

Arakawa, Akiko et al., "Unopposed IL-36 Activity Promotes Clonal CD4+ T-Cell Responses with IL-17A Production in Generalized Pustular Psoriasis," *Journal of Investigative Dermatology* (Corrected proof published online Mar. 13, 2018); 138:1338-1347.

Asadollahi, Tahereh et al., "QSAR Models for CXCR2 Receptor Antagonists Based on the Genetic Algorithm for Data Preprocessing Prior to Application of the PLS Linear Regression Method and Design of the New Compounds Using In Silico Virtual Screening," *Molecules* (Feb. 25, 2011); 16:1928-1955.

Barbosa, Maria Leticia de Castro et al., "Therapeutic approaches for tumor necrosis factor inhibition," *Brazilian Journal of Pharmaceutical Sciences* (Jul./Sep. 2011; accepted for pub May 25, 2011); 47:427-446.

Bassoy, Esen Yonca et al., "Regulation and function of interleukin-36 cytokines," *Immunological Reviews* (2018); 281:169-178. https://doi.org/10.1111/imr.12610.

Benjegerdes, Katie E. et al., "Pustular psoriasis: pathophysiology and current treatment perspectives," *Psoriasis: Targets and Therapy* (Sep. 12, 2016); 6:131-144.

Biju, Purakkattle et al., "3,4-Diamino-2,5-thiadiazole-1-oxides as potent CXCR2/CXCR1 antagonists," *Bioorganic & Medicinal Chemistry Letters* (2008; available online Oct. 30, 2007); 18:228-231.

Biju, Purakkattle et al., "Fluoroalkyl α side chain containing 3,4-diamino-cyclobutenediones as potent and orally bioavailable CXCR2-CXCR1 dual antagonists," *Bioorganic & Medicinal Chemistry Letters* (available online Jan. 15, 2009); 19:1431-1433.

Biju, Purakkattle et al., "3,4-Diamino-1,2,5-thiadizole as potent and selective CXCR2 antagonists," *Bioorganic & Medicinal Chemistry Letters* (available online Jan. 15, 2009); 19:1434-1437.

Blumberg, Hal et al., "Opposing activities of two novel members of the IL-1 ligand family regulate skin inflammation," *The Journal of Experimental Medicine* (Oct. 29, 2007); 204(11):2603-2614; Supp Info: http://doi.org/10.1084/jem.20070157.

Borges-Costa, João et al., "Clinical and Laboratory Features in Acute Generalized Pustular Psoriasis, A Retrospective Study of 34 Patients," *Am J. Clin Dermatol* (2011; first online Aug. 21, 2012); 12(4):271-276.

Bridgewood, Charlie et al., "IL-36$^\gamma$ Is a Strong inducer of IL-23 in Psoriatic Cells and Activates Angiogenesis," *Frontiers in Immunology* (Feb. 26, 2018) 9(200); 14 pages.

Busch-Petersen, Jakob et al., "Phenol-containing antagonists of the CXCR2 receptor," *Expert Opin. Ther. Patents* (published online May 26, 2008); 18(6):629-637.

Cai, Yihua et al., "Pivotal Role of Dermal IL-17-Producing $\gamma\delta$ T Cells in Skin Inflammation," *Immunity* (Oct. 28, 2011); 35:596-610.

Campbell, James J. et al., "IL-17-Secreting $\gamma\delta$ T Cells Are Completely Dependent upon CCR6 for Homing to Inflamed Skin," *The Journal of Immunology* (Prepublished online Sep. 29, 2017); 199:3129-3136.

Chao, Jianhua et al., "C(4)-alkyl substituted furanyl cyclobutenediones as potent, orally bioavailable CXCR2 and CXCR1 receptor antagonists," *Bioorganic & Medicinal Chemistry Letters* (available online Apr. 10, 2007); 17:3778-3783.

Cook, Donald N. et al., "CCR6 Mediates Dendritic Cell Localization Lymphocyte Homeostasis, and Immune Responses in Mucosal Tissue," *Immunity* (May 2000; revised Apr. 18, 2000); 12:495-503.

Cullberg, Marie et al., "Pharmacokinetics of the Oral Selective CXCR2 Antagonist AZD5069: A Summary of Eight Phase I Studies in Healthy Volunteers," *Drugs R D* (published online May 31, 2018); 18:149-159.

Dwyer, Michael P. et al., "Discovery of 2-Hydrozy-N,N-dimethyl-3-{2-[[(R)-1-(5-methylfuran-2-yl)propyl]amino]-3,4-dioxo-cyclobut-1-enylamino}benzamide (SCH 527123): A Potent, Orally Bioavailable CXCR2/CXCR1 Receptor Antagonist," *J. Med. Chem.* (Aug. 9, 2006); 49(26):7603-7606.

Ebsworth, Karen et al., "Chemokine Receptor Inhibition as a Novel Therapeutic Approach for Psoriasis," *Poster No. 521* ChemoCentryx, Inc., Mountain View, CA (May 12, 2016); 2 pages.

Foster, Alexander M. et al., "IL36 Promotes Myeloid Cell Infiltration, Activation, and Inflammatory Activity in Skin," *The Journal of Immunology* (published online May 14, 2014); 192; 10 pages.

Furue, Kazuhisa et al., "Highlighting Interleukin-36 Signalling in Plaque Psoriasis and Pustular Psoriasis," *Acta Derm Venereol* (2018; Epub ahead of print Oct. 2, 2017); 98; 9 pages.

Gunda, Shravan Kumar et al., "Structural investigations of CXCR2 receptor antagonists by CoMFA, CoMSIA and flexible docking studies," *Acta Pharm* (Jul. 17, 2012); 62:287-304.

Imafuku, Shinichi et al., "Efficacy and safety of secukinumab in patients with generalized pustular psoriasis: A 52-week analysis from phase III open-label multicenter Japanese study," *Journal of Dermatology* (2016; Accepted Dec. 18, 2015); 43:1011-1017.

Kucharzik, Torsten et al., "CCR6 expression distinguishes mouse myeloid and lymphoid dendritic cell subsets: demonstration using a CCR6 EGFP knock-in mouse," *Eur. J. Immunol.* (2002; Accepted Oct. 16, 2001); 32:104-112.

(56) References Cited

OTHER PUBLICATIONS

Lai, Gaifa et al., "Synthesis and structure-activity relationships of new disubstiuted phenyl-containing 3,4-diamino-3-cyclobutene-1,2-diones as CXCR2 receptor antagonists," *Bioorganic & Medicinal Chemistry Letters* (available online Feb. 10, 2008); 18:1864-1868.

Liu, Shilan et al., "Design, synthesis, and evaluation of novel 3-amino-4-hydrazine-cyclobut-3-ene-1,2-diones as potent and selective CXCR2 chemokine receptor antagonists," *Bioorganic & Medicinal Chemistry Letters* (available online Aug. 7, 2009); 19:5741-5745.

Mahil, Satveer K. et al., "Update on psoriasis immunopathogenesis and targeted immunotherapy," *Semin Immunopathol* (2016; published online Nov. 16, 2015); 38:11-27.

Mansouri, Bobbak et al., "Biological therapies for psoriasis," *Expert Opinion on Biological Therapy* (published online Oct. 28, 2013); 13(12):1715-1730.

Marrakchi, Slaheddine, M.D., Ph.D., et al., "Interleukin-36-Receptor Antagonist Deficiency and Generalized Pustular Psoriasis," *The New England Journal of Medicine* (Aug. 18, 2011); 365(7):620-628.

Mccleland, Brent W. et al., "Comparison of N,N'-diarylsquaramides and N,N'-diarylureas as antagonists of the CXCR2 chemokine receptor," *Bioorganic & Medicinal Chemistry Letters* (2007; available online Dec. 23, 2006); 17:1713-1717.

Merad, Miriam et al., "The Dendritic Cell Lineage: Ontogeny and Function of Dendritic Cells and Their Subsets in the Steady State and the Inflamed Setting," *Annu Rev Immuno.* (Dec. 6, 2013); 31; 48 pages.

Merritt, J. Robert et al., "Synthesis and structure-activity relationships of 3,4-diaminocyclobut-3-ene-1,2-dione CXCR2 antagonists," *Bioorganic & Medicinal Chemistry Letters* (available online May 11, 2006); 16:4107-4110.

Milora, Katelynn A. et al., Unprocessed Interleukin-36α Regulates Psoriasis-Like Skin Inflammation in Cooperation with Interleukin-1, *Journal of Investigative Dermatology* (published online Aug. 13, 2015); 135:2992-3000.

Müller, Anne et al., "IκBζ is a key transcriptional regulator of IL-36-driven psoriasis-related gene expression in keratinocytes," *PNAS Latest Articles* (accepted by Editorial Board Aug. 17, 2018); received for review Jan. 24, 2018); www.pnas.org/cgi/doi/10.1073/pnas.1801377115; 6 pages.

Naik, Haley B. et al., "Autoinflammatory Pustular Neutrophilic Diseases," *Dermatol Clin.* (Jul. 2013); 31(3):405-425. doi:10.1016/j.det.2013.04.001.

Navarini, A. A. et al., "European consensus statement on phenotypes of pustular psoriasis," *J EurAcad Dermatol Venereol* (Accepted May 18, 2017); 31:1792-1799.

Nieuwenhuis, S. A. M. et al., "Structure of the $Y_D$ Tyrosine Radical in Photosystem II. Determination of the Orientation of the Phenoxyl Ring by Enantioselective Deuteration of the Methylene Group," *J. Am. Chem. Soc.* (Jan. 16, 1998); 120:829-830.

Onoufriadis, Alexandros et al., "Mutations in IL36RN/IL1F5 Are Associated with the Severe Episodic Inflammatory Skin Disease Known as Generalized Pustular Psoriasis, *The American Journal of Human Genetics*," (Sep. 9, 2011); 89:432-437.

Rennard, Stephen I. et al., "CXCR2 Antagonist MK-7123," *Am J Respir Crit Care Med* (May 1, 2015); 191(9):1001-1011.

Robinson, Amanda, M.D. et al., "Treatment of pustular psoriasis: From the Medical Board of the National Psoriasis Foundation," *J Am Acad Dermatol* (Aug. 2012; published online May 21, 2012); 67:279-288.

Schall, Thomas J. et al., "Overcoming hurdles in developing successful drugs targeting chemokine receptors," *Nature Reviews Immunology* (May 2011; published online Apr. 15, 2011); 11:355-363.

Swindell, William R. et al., "Imiquimod has strain-dependent effects in mice and does not uniquely model human psoriasis," *Genome Medicine* (Published online Mar. 9, 2017); 9:24; 21 pages.

Tortola, Luigi et al., "Psoriasiform dermatitis is driven by IL-36-mediated DC-keratinocyte crosstalk," *The Journal of Clinical Investigation* (Nov. 2012; accepted in revised form Aug. 30, 2012); 122(11 ):3965-3976.

Towne, Jennifer E. et al., "Interleukin-36 (IL-36) Ligands Require Processing for Full Agonist (IL-36α, IL-36β, and IL-36$^\gamma$) or Antagonist (IL-36Ra) Activity," *The Journal of Biological Chemistry* (Dec. 9, 2011); 286(49):42594-42602.

Van Der Fits, Leslie et al., "Imiquimod-Induced Psoriasis-Like Skin Inflammation in Mice is Mediated via the IL-23/IL-17 Axis," *The Journal of Immunology* (Accepted for publication Feb. 23, 2009); 182:5836-5845.

Varona, Rosa et al., "CCR6-deficient mice have impaired leukocyte homeostasis and altered contact hypersensitivity and delayed-typed hypersensitivity responses," *The Journal of Clinical Investigation* (2001; Accepted and revised Dec. 11, 2000); 107(6):R37-R45.

Wijtmans, Maikel et al., "Therapeutic targeting of chemokine receptors by small molecules," *Drug Discovery Today: Technologies* (2012; http://dx.doi.org/10.1016/j.ddtec.2012.03.004); 9(4):e229-e236.

Yu, Younong et al., "Synthesis and structure-activity relationships of heteroaryl substituted-3,4-diamino-3-cyclobut-3-ene-1,2-dione CXCR2/CXCR1 receptor antagonists," *Bioorganic & Medicinal Chemistry Letters* (available online Jan. 11, 2008); 18:1318-1322.

Zhang, Shuang et al., "Comparative Analysis of Pharmacophore Features and Quantitative Structure-Activity Relationships for CD38 Covalent and Non-covalent Inhibitors," *Chemical Biology & Drug Design* (Dec. 2015; first published Jul. 14, 2015); 86(6):1411-1424.

Zhou, Yi et al., "Design, Synthesis and Biological Evaluation of Noncovalent Inhibitors of Human CD38 NADase," *ChemMedChem* (Feb. 6, 2012); 7(2):223-228.

European Search Report corresponding to EP 16867098.2 dated Jun. 5, 2019.

Campbell, James J. et al., "Efficacy of Chemokine Receptor Inhibition in Treating IL-36 α-Induced Psoriasiform Inflammation," *J. Immunol* (2019; pre-published online Feb. 4, 2019); 202:1687-1692.

\* cited by examiner 1.004 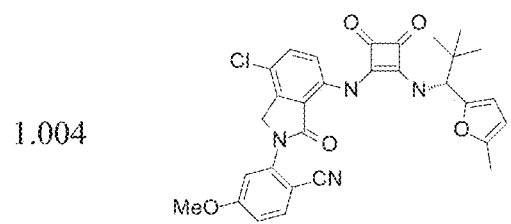
1.005 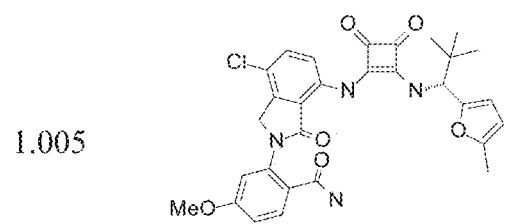
1.006 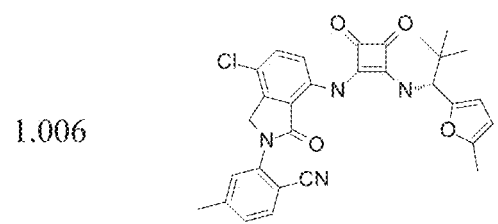
1.007 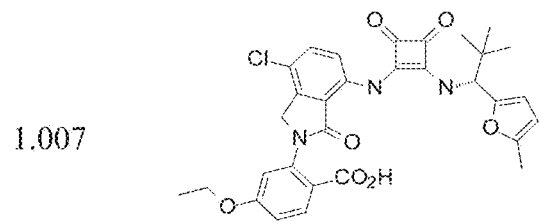
1.008 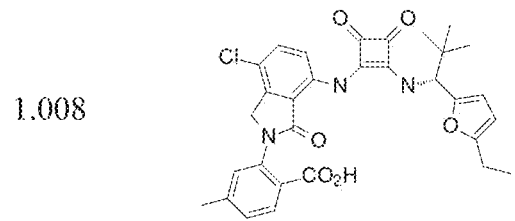
FIG. 1B 1.009 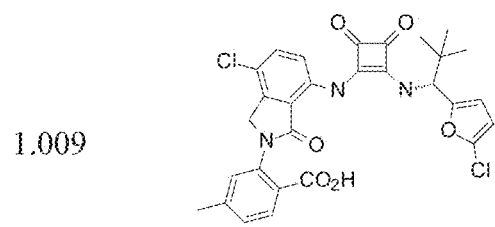
1.010 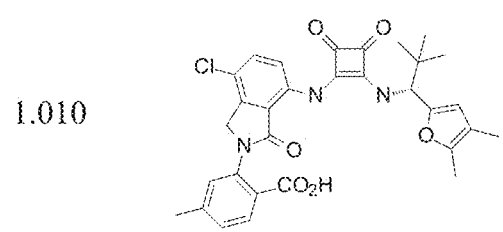
1.011 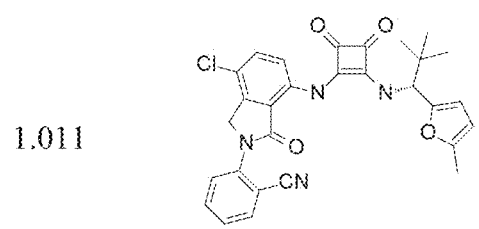
1.012 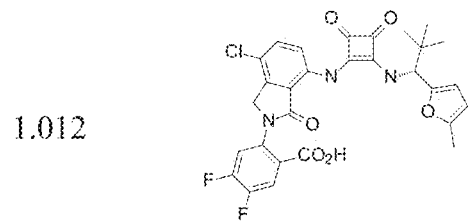
1.013 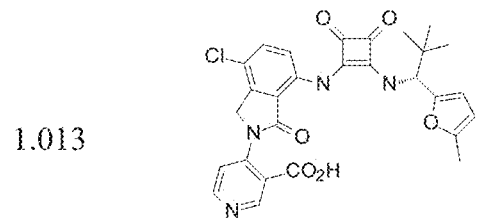
FIG. 1C 1.014 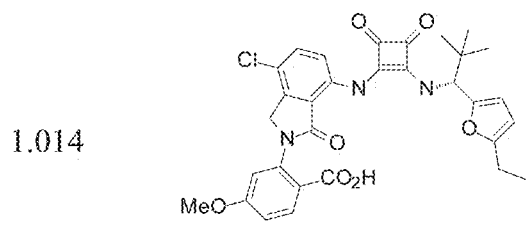
1.015 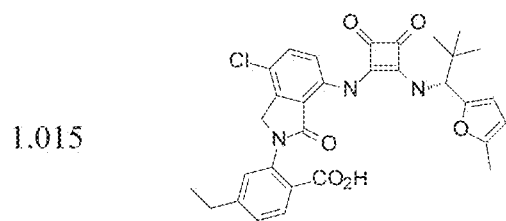
1.016 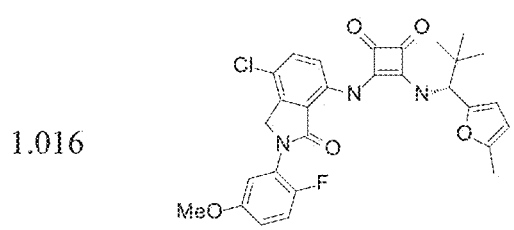
1.017 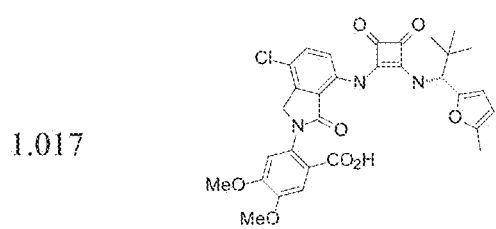
1.018 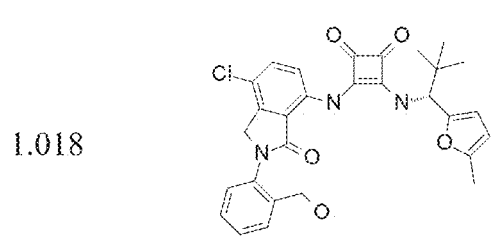
FIG. 1D 1.019 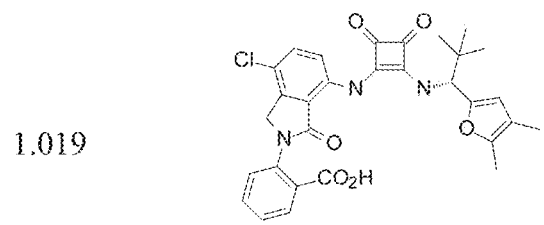
1.020 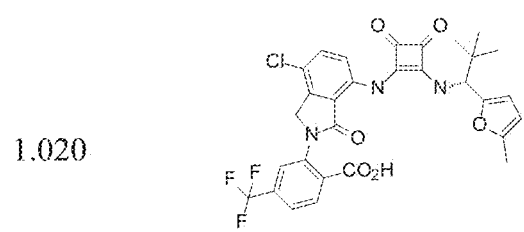
1.021 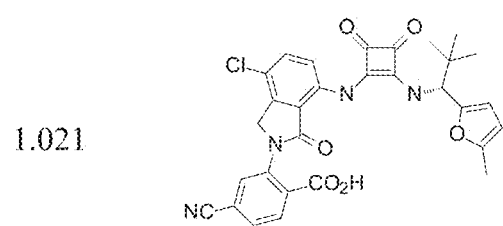
1.022 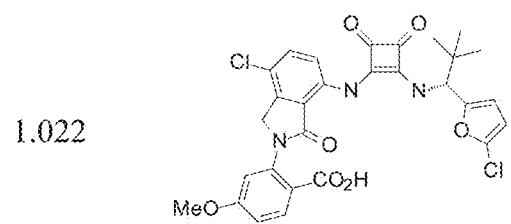
1.023 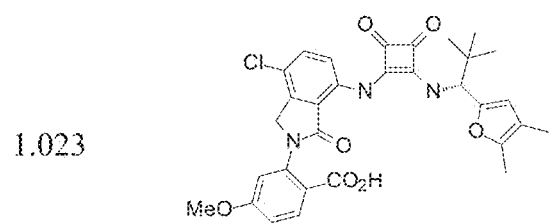
FIG. 1E 1.024 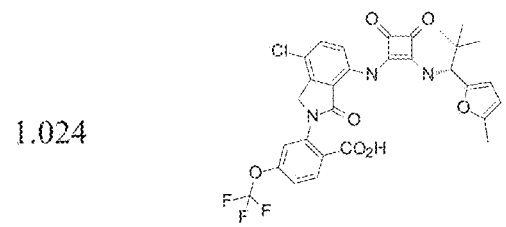
1.025 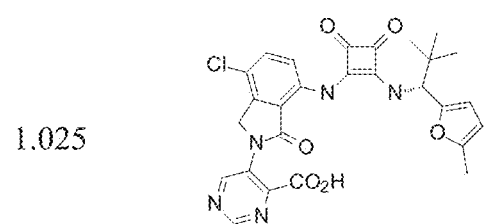
1.026 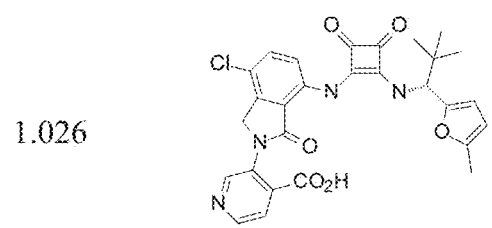
1.027 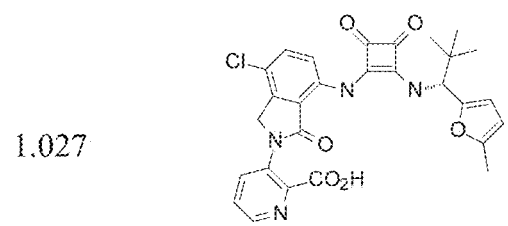
1.028 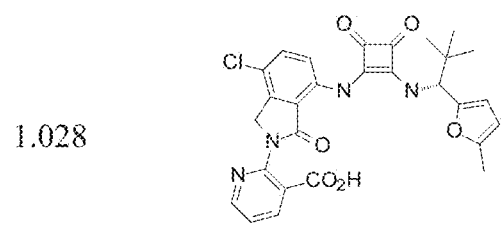
FIG. 1F 1.029 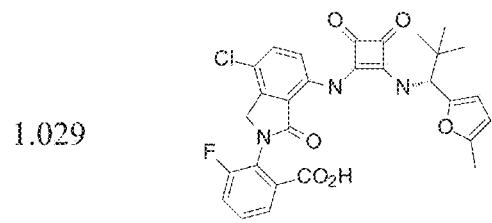
1.030 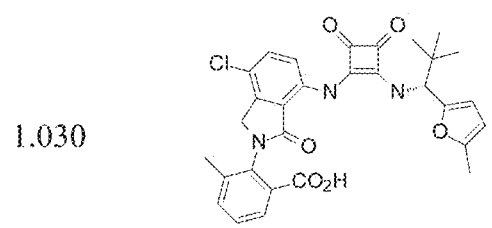
1.031 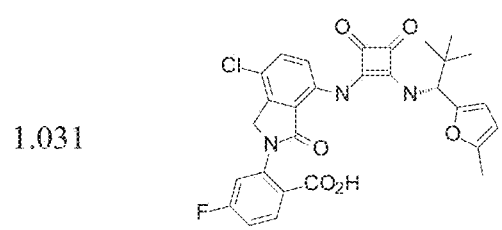
1.032 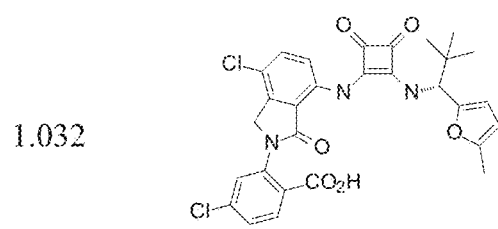
1.033 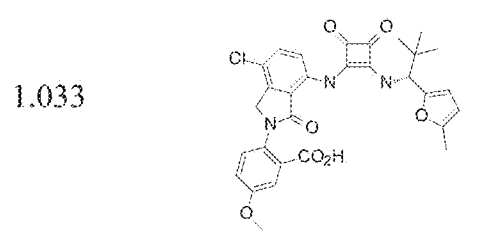
FIG. 1G 1.034 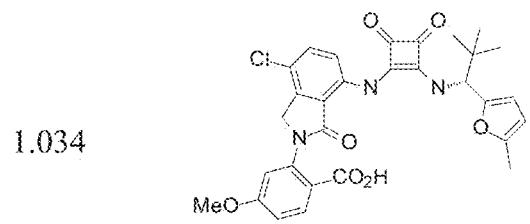
1.035 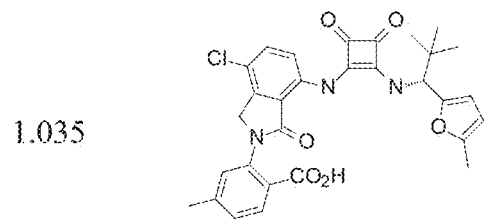
1.036 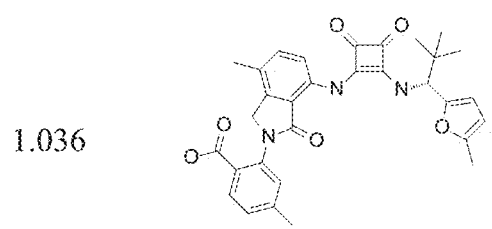
1.037 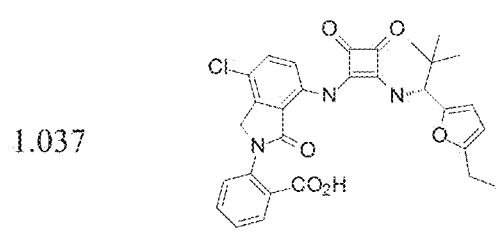
1.038 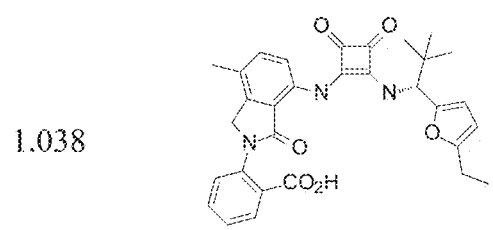
FIG. 1H 1.044 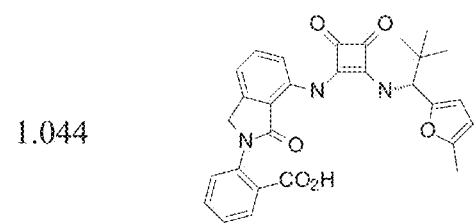
1.045 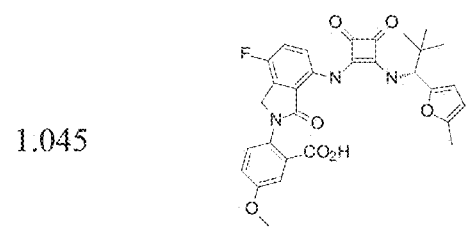
1.046 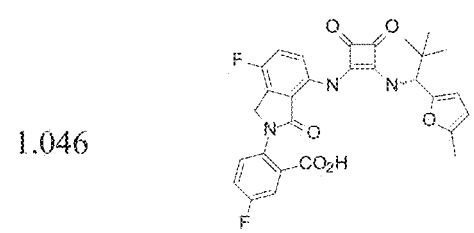
1.047 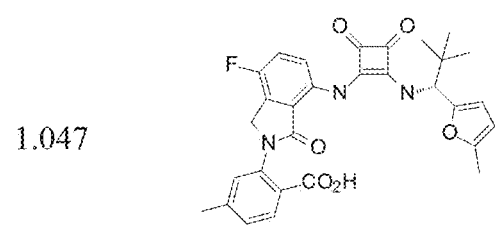
1.048 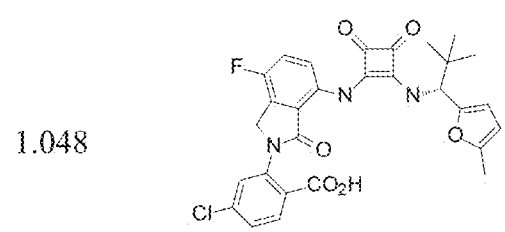
FIG. 1J 1.049 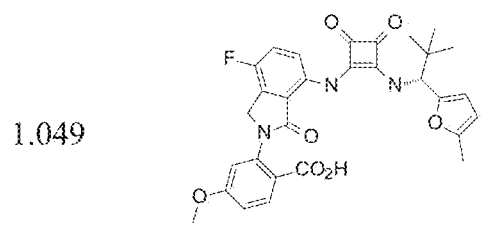
1.050 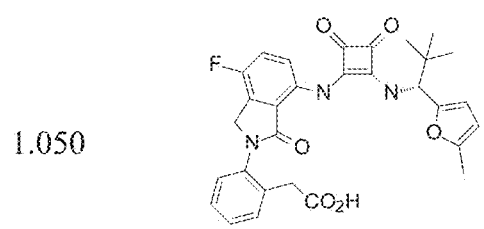
1.051 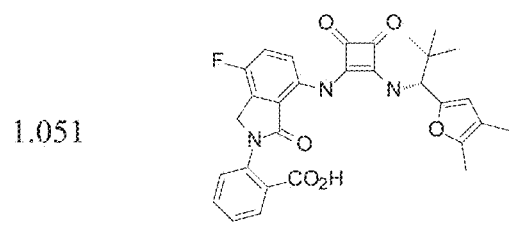
1.052 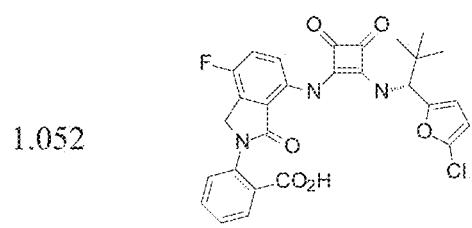
1.053 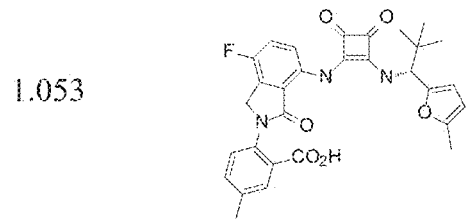
FIG. 1K 1.054 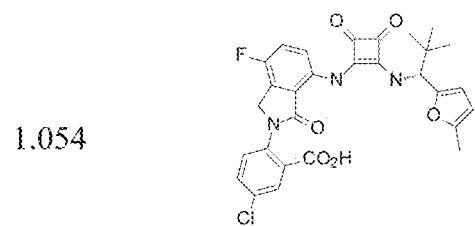
1.055 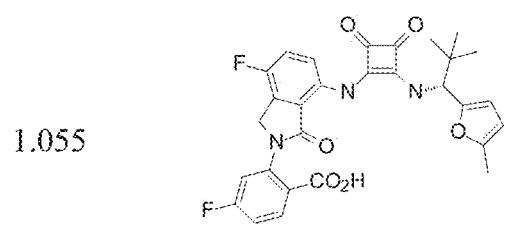
1.056 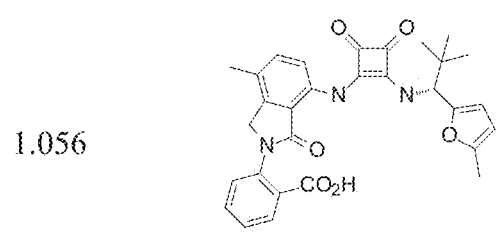
1.057 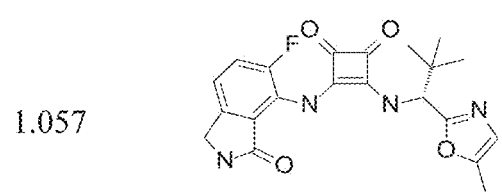
1.058 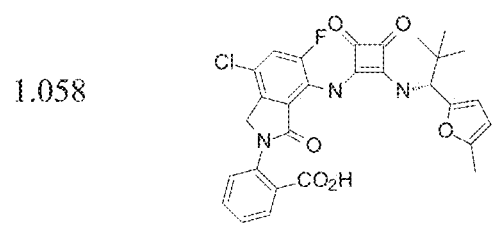
FIG. 1L 1.059 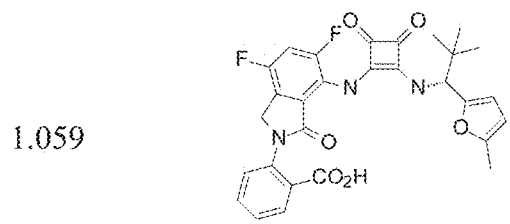
1.060 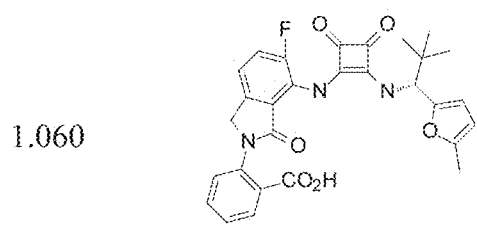
1.061 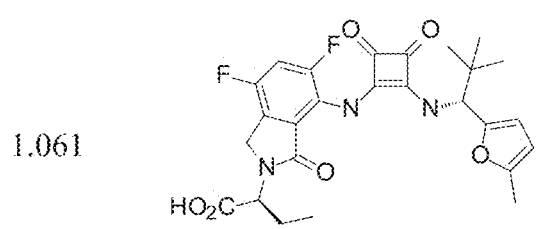
1.062 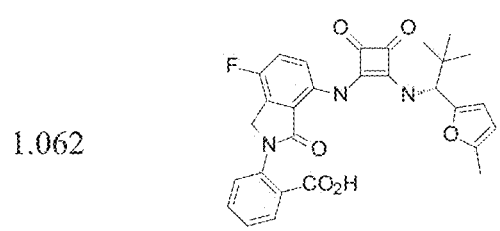
1.063 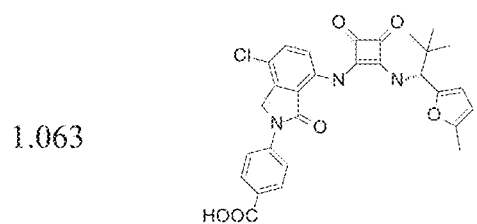
FIG. 1M 1.064 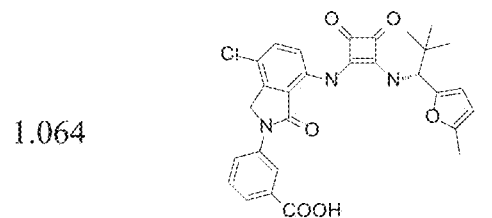
1.065 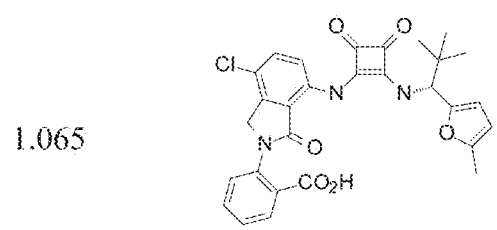
1.066 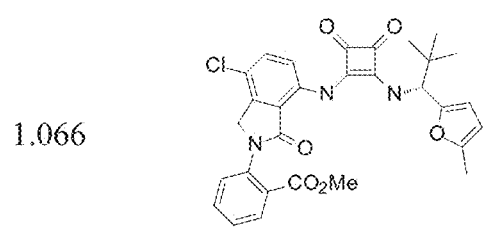
1.067 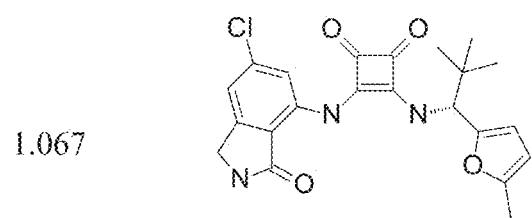
1.068 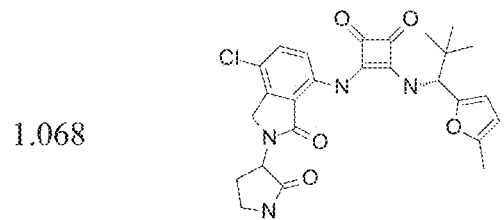
FIG. 1N 1.069 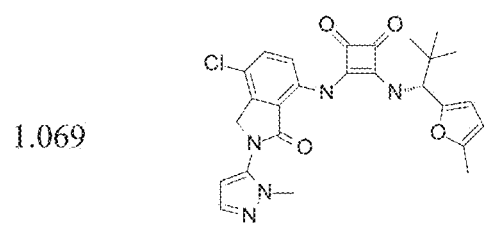
1.070 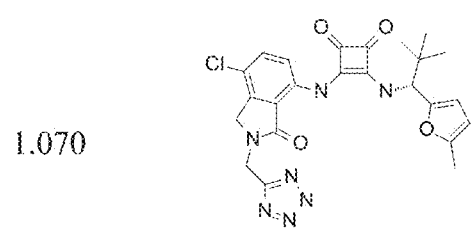
1.071 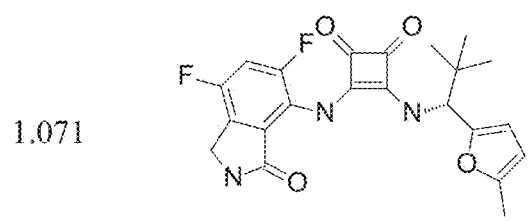
1.072 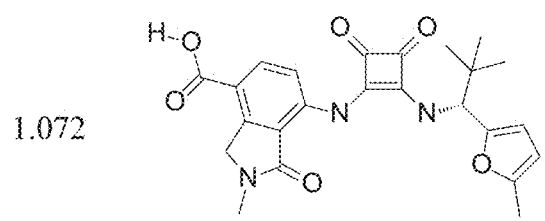
1.073 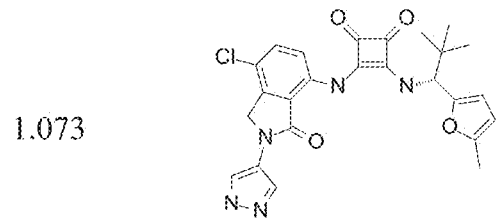
FIG. 10

1.074 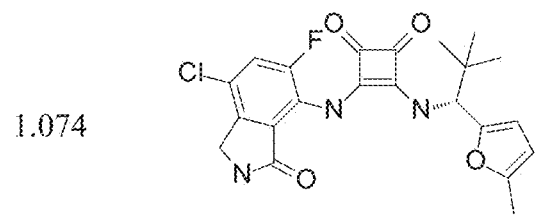
1.075 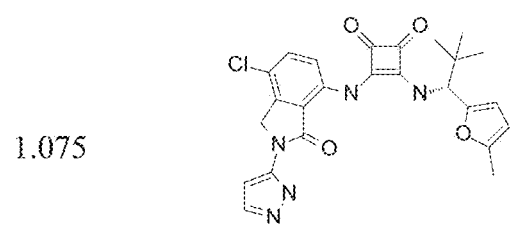
1.076 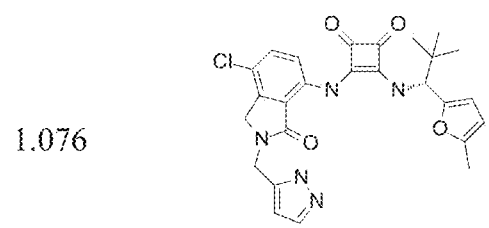
1.077 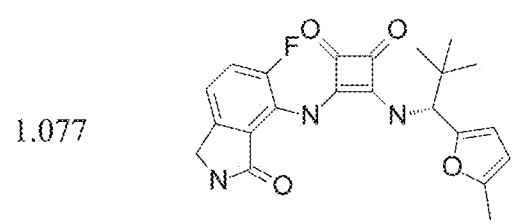
1.078 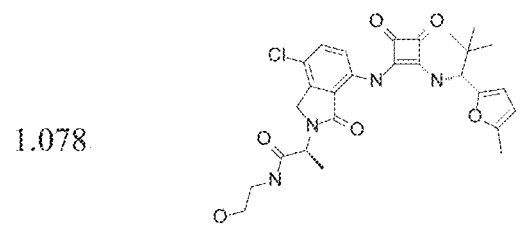
FIG. 1P 1.079 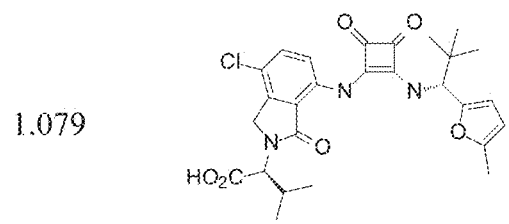
1.080 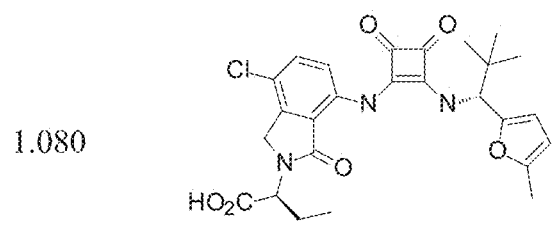
1.081 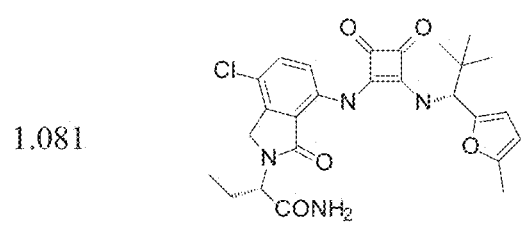
1.082 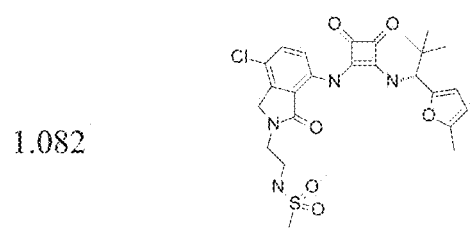
1.083 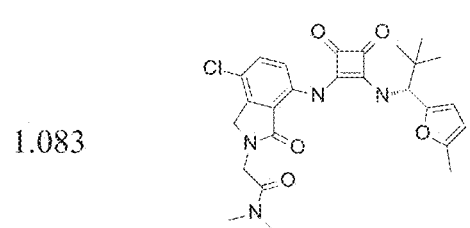
FIG. 1Q 1.084 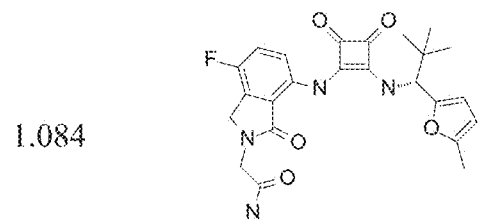
1.085 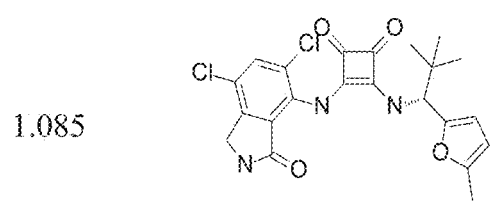
1.086 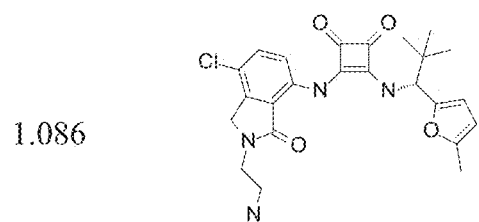
1.087 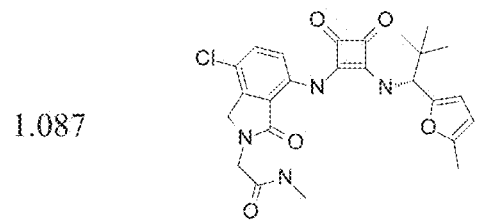
1.088 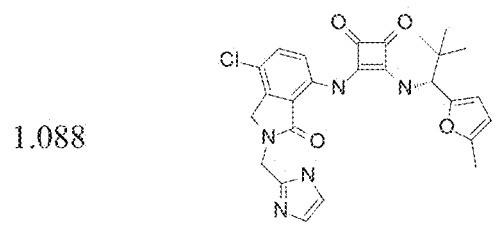
FIG. 1R 1.089 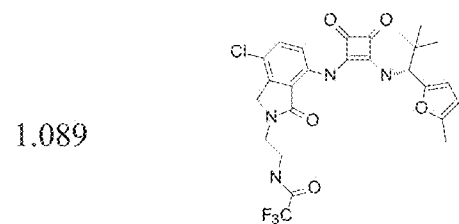
1.090 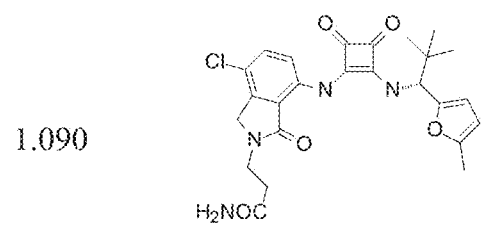
1.091 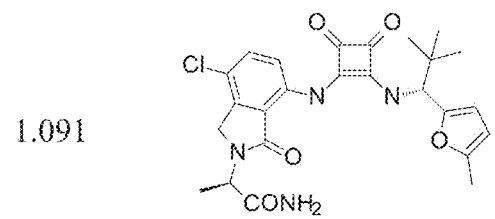
1.092 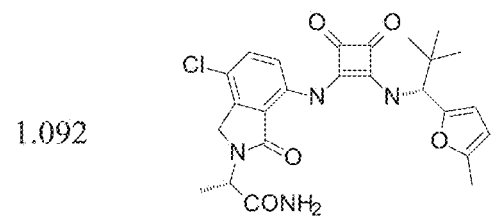
1.093 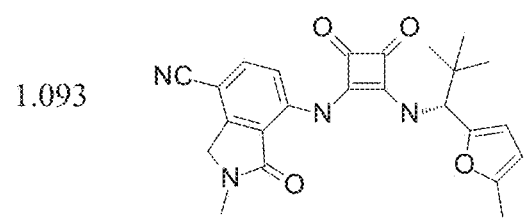
FIG. 1S 1.094 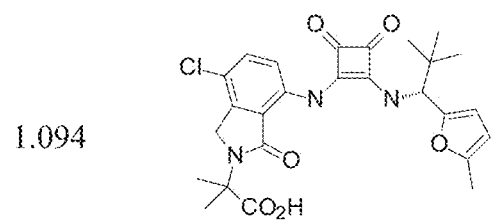
1.095 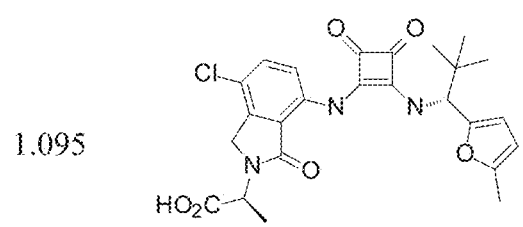
1.096 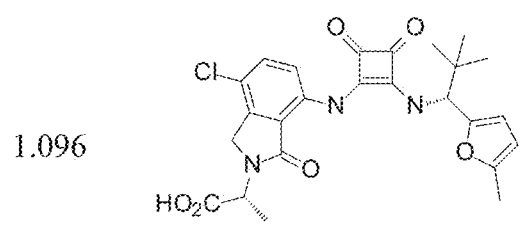
1.097 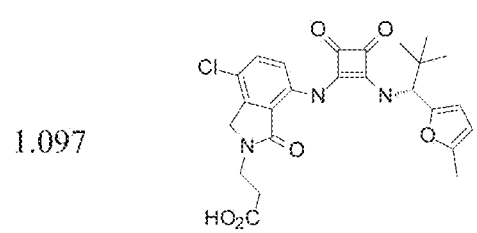
1.098 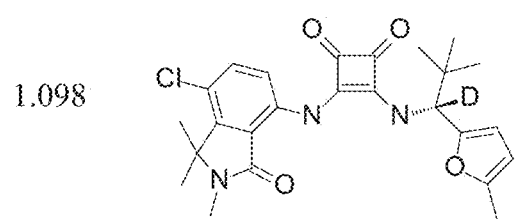
FIG. 1T 1.099 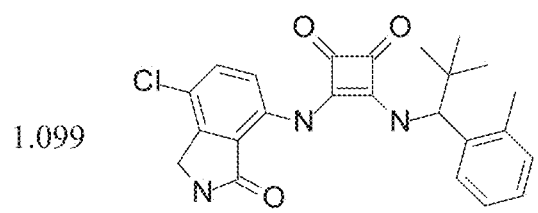
1.100 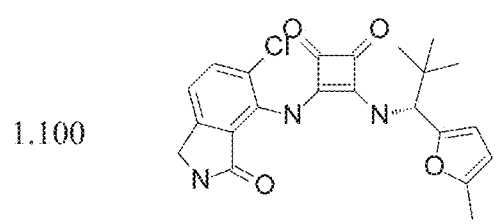
1.101 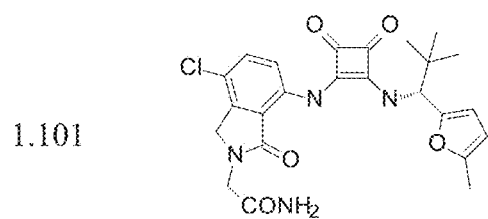
1.102 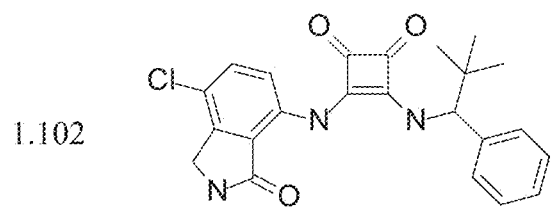
1.103 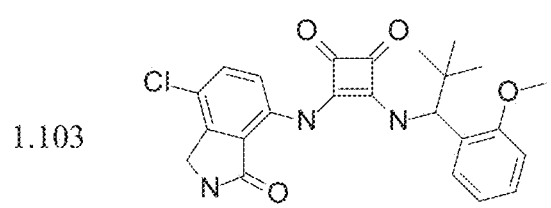
FIG. 1U 1.104 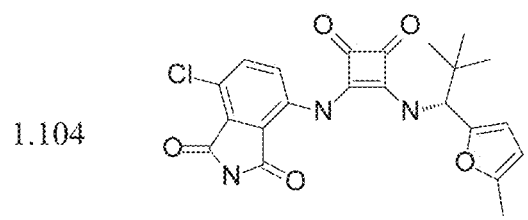
1.105 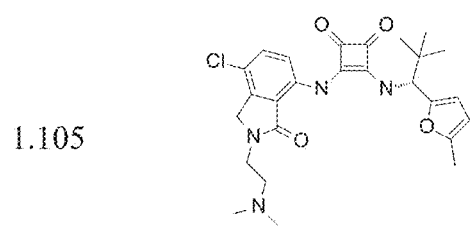
1.106 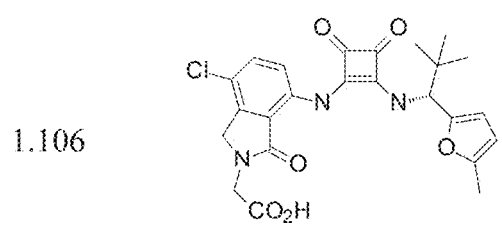
1.107 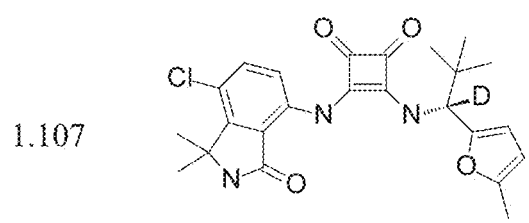
1.108 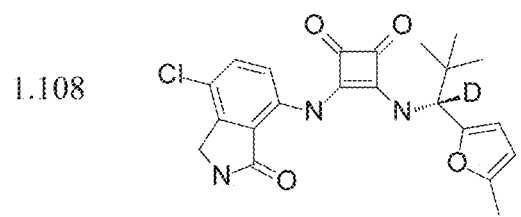
FIG. IV 1.109 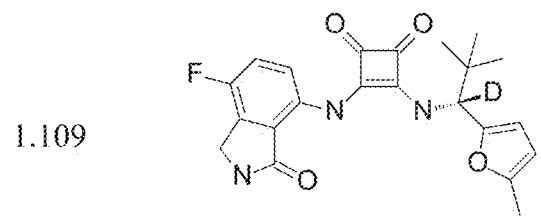
1.110 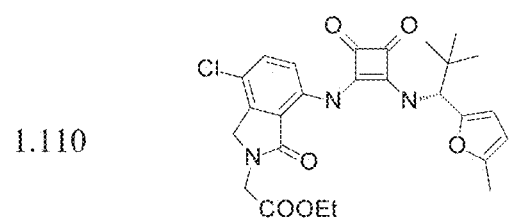
1.111 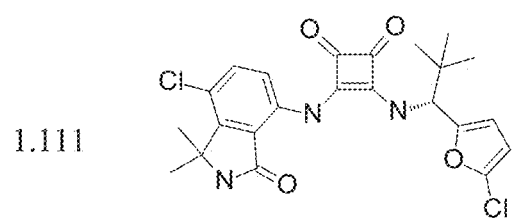
1.112 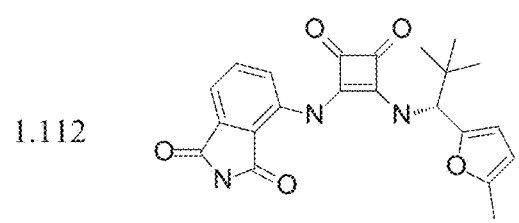
1.113 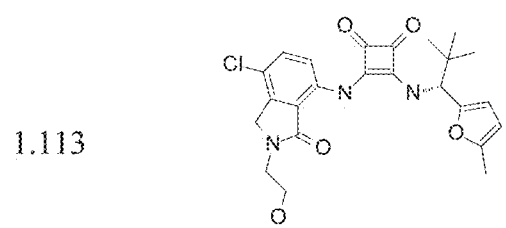
FIG. 1W 1.114 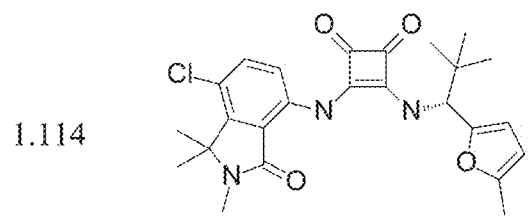
1.115 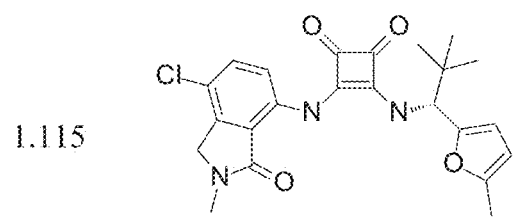
1.116 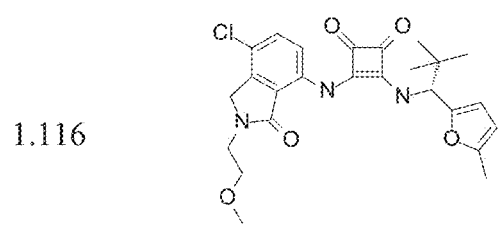
1.117 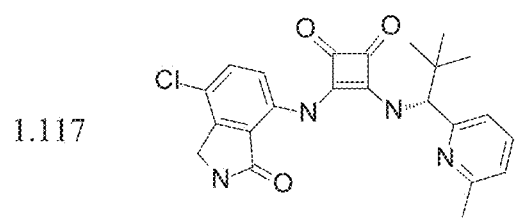
1.118 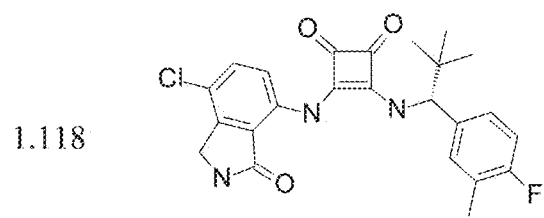
FIG. 1X 1.119 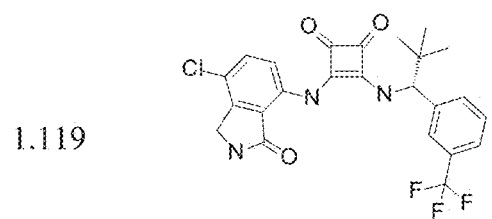
1.120 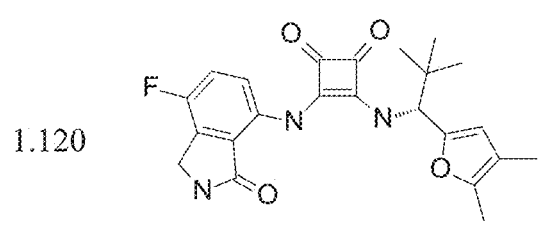
1.121 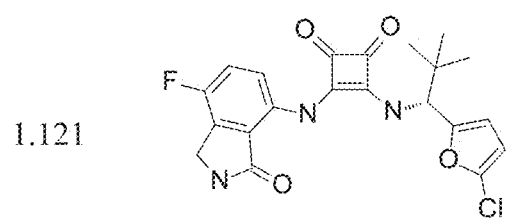
1.122 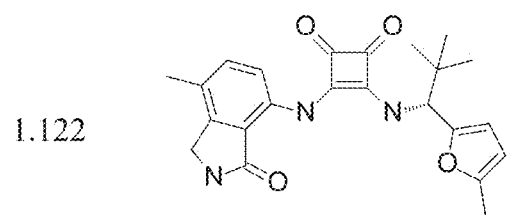
1.123 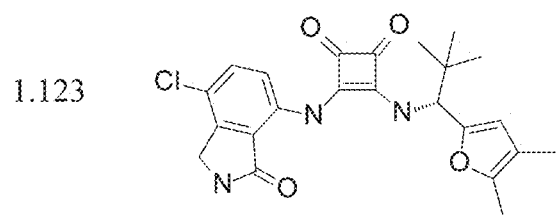
FIG. 1Y 1.124 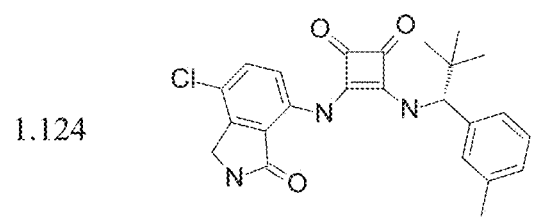
1.125 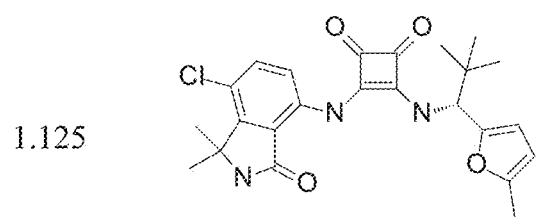
1.126 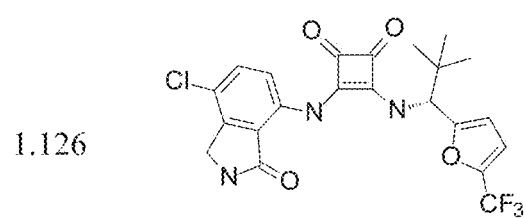
1.127 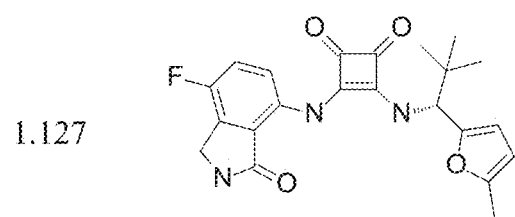
1.128 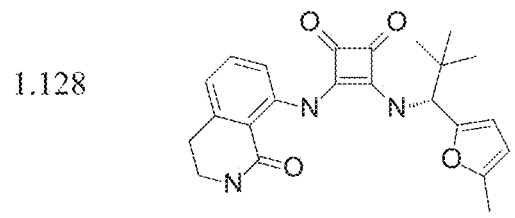
FIG. 1Z 1.129 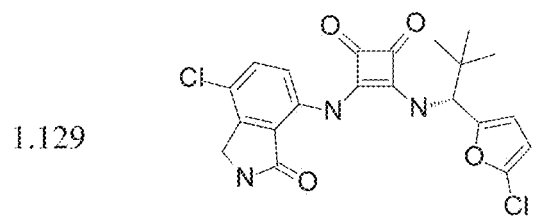
1.130 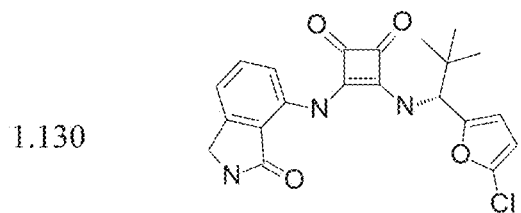
1.131 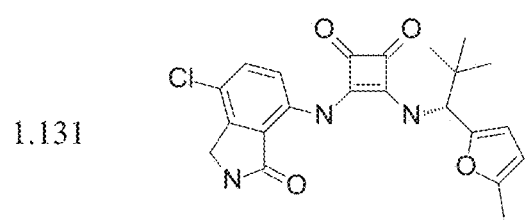
1.132 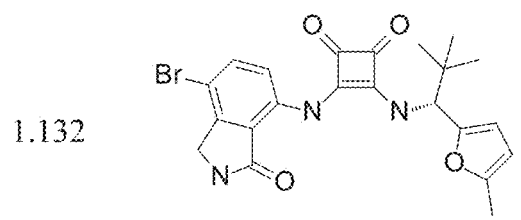
1.133 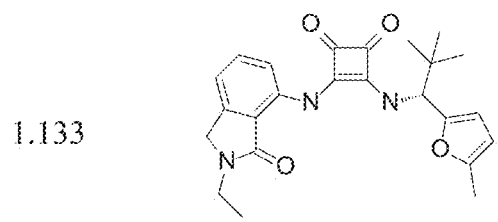
FIG. 1AA 1.134 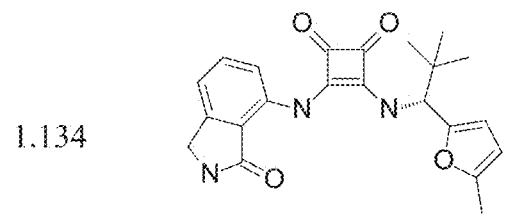
1.135 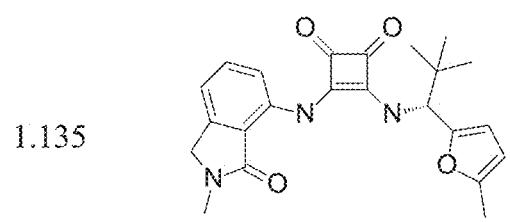
1.136 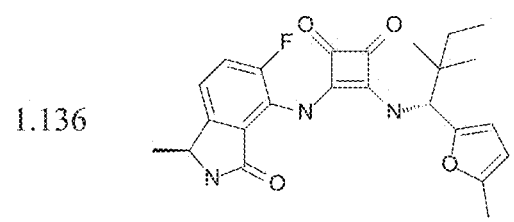
1.137 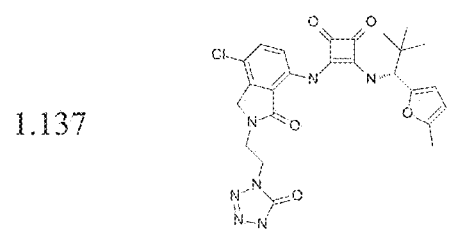
1.138 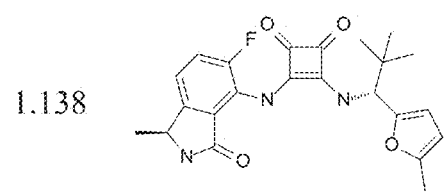
FIG. 1AB 1.139 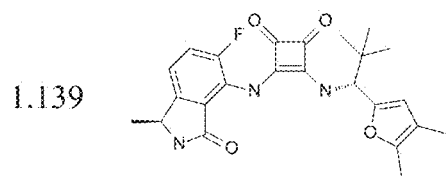
1.140 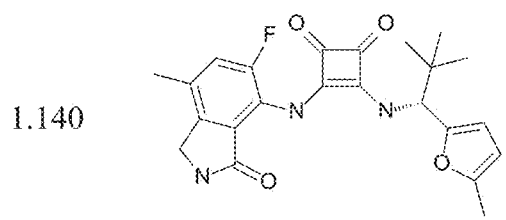
1.141 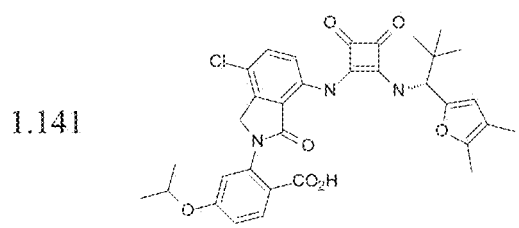
1.142 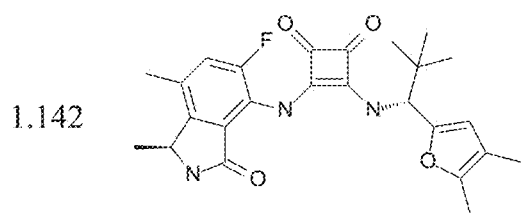
1.143 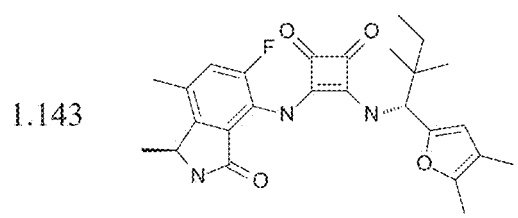
1.144 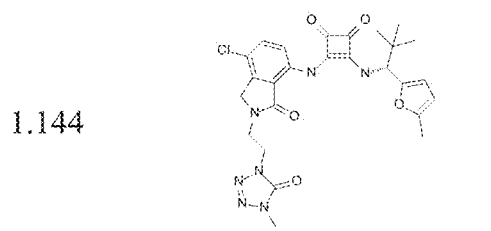
FIG. 1AC 1.145 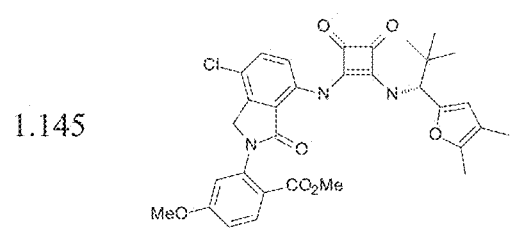
1.146 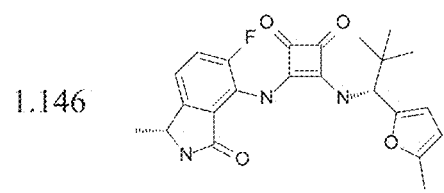
1.147 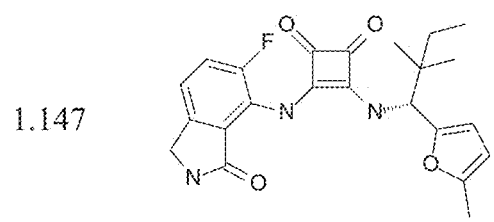
1.148 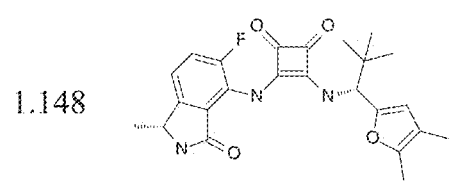
1.149 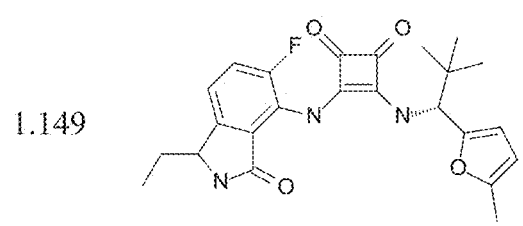
1.150 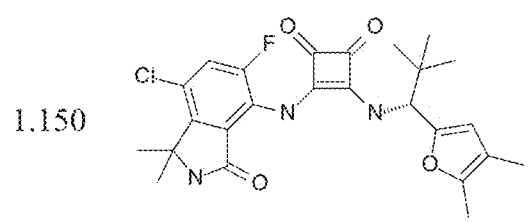
FIG. 1AD 1.151 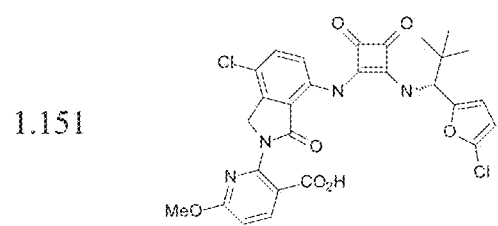
1.152 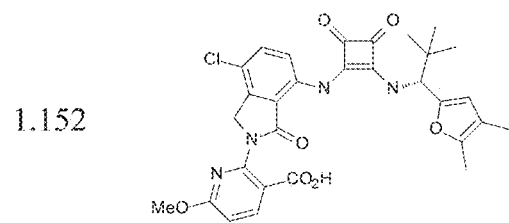
1.153 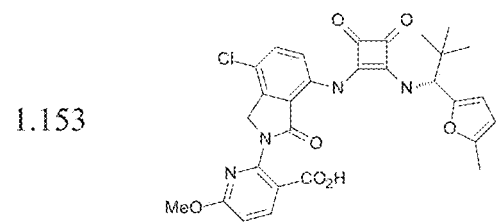
1.154 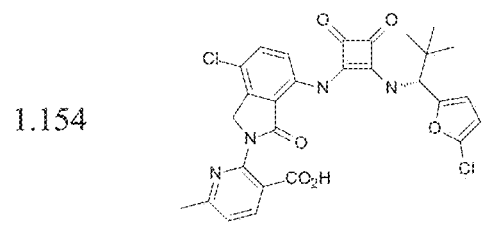
1.155 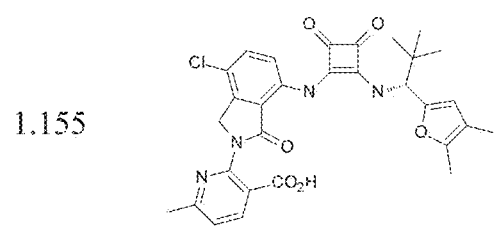
1.156 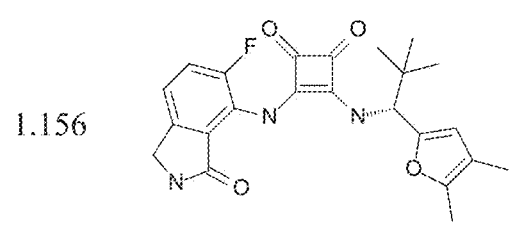
FIG. 1AE 1.157 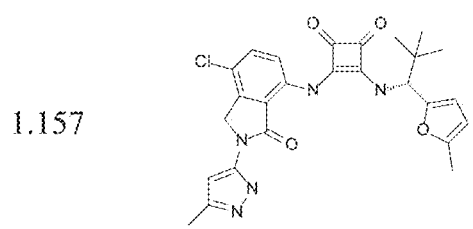
1.158 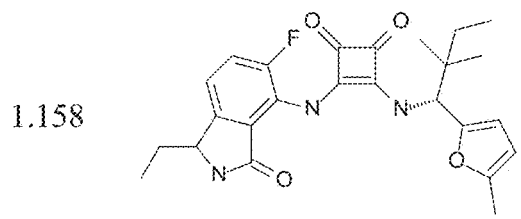
1.159 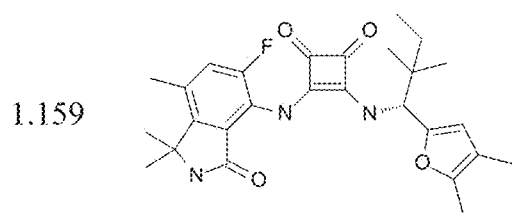
1.160 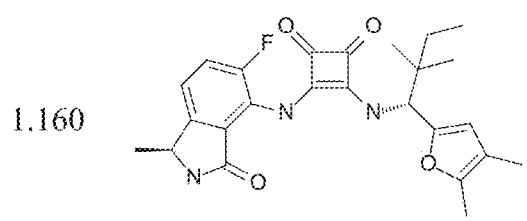
1.161 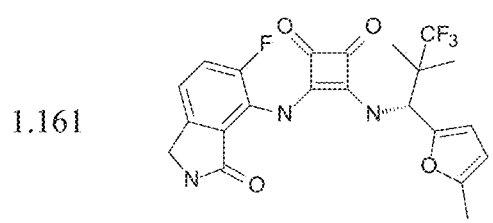
1.162 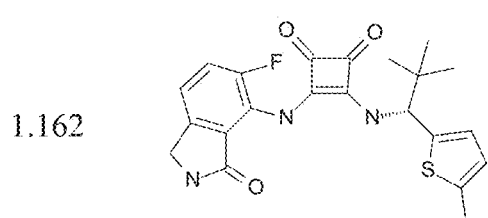
FIG. 1AF 1.163 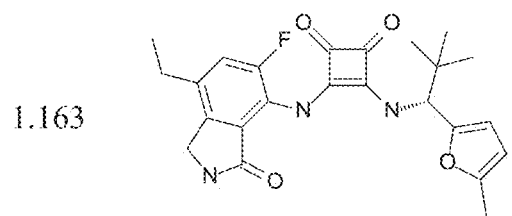
1.164 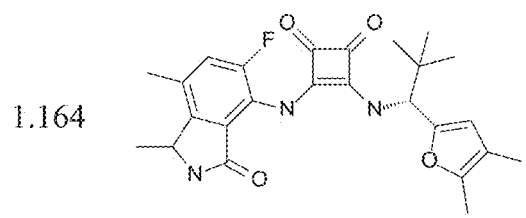
1.165 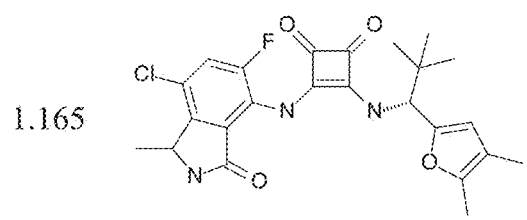
1.166 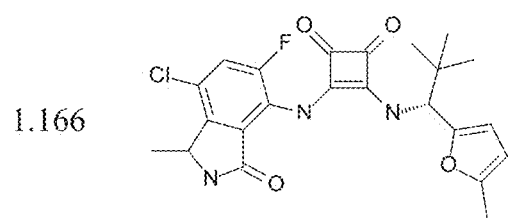
1.167 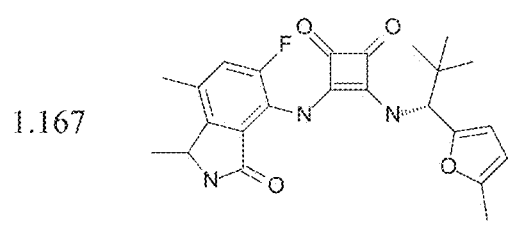
1.168 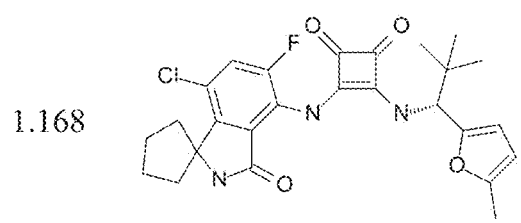
FIG. 1AG 1.169 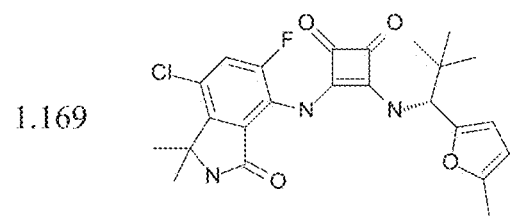
1.170 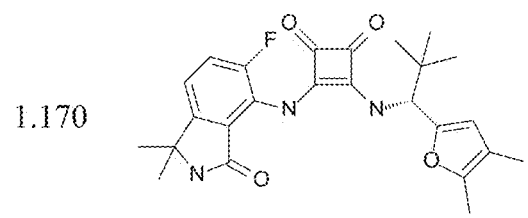
1.171 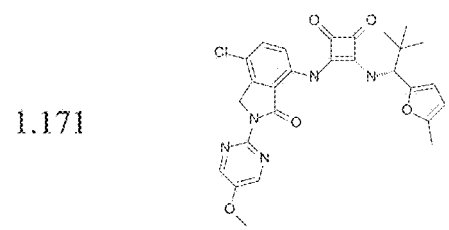
1.172 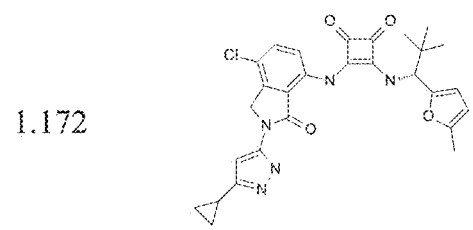
1.173 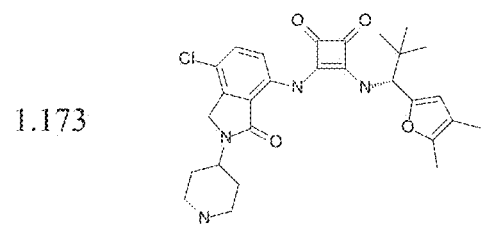
1.174 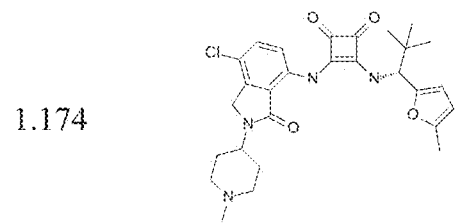
FIG. 1AH 1.175 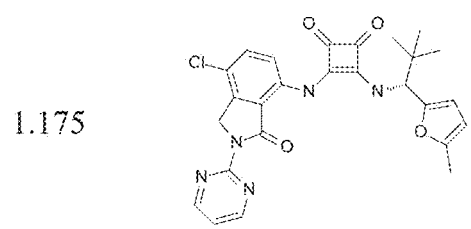
1.176 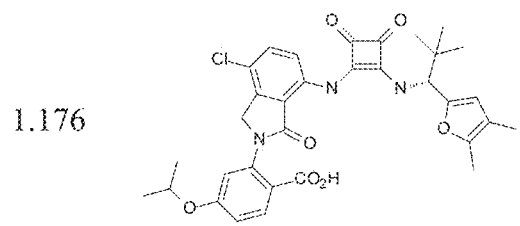
1.177 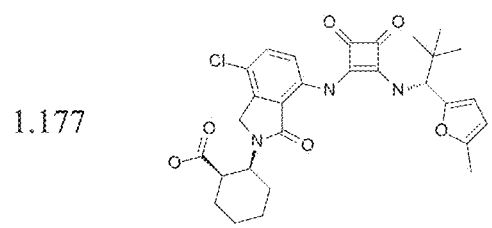
1.178 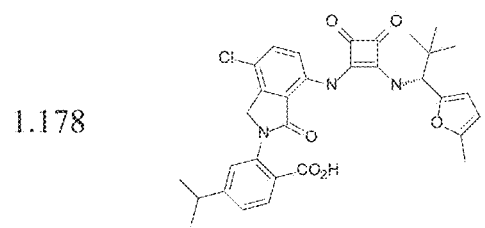
1.179 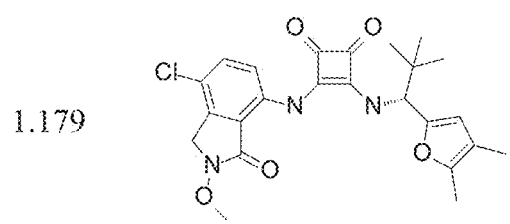
1.180 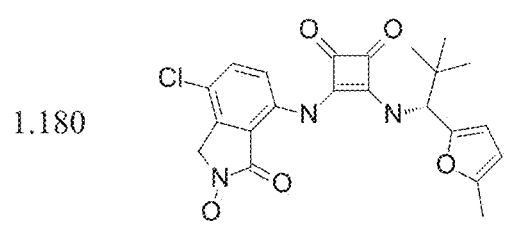
FIG. 1AI 1.181 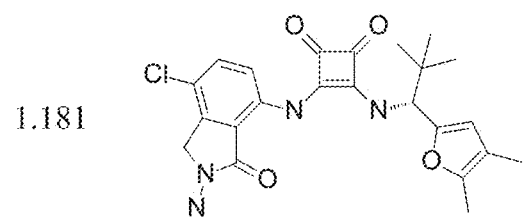
1.182 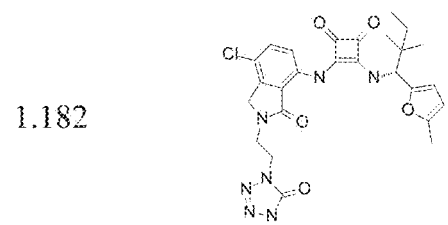
1.183 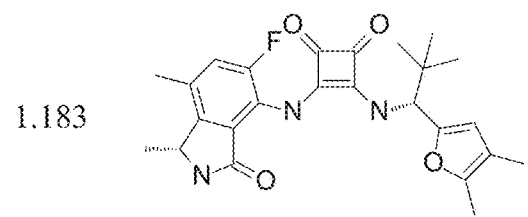
1.184 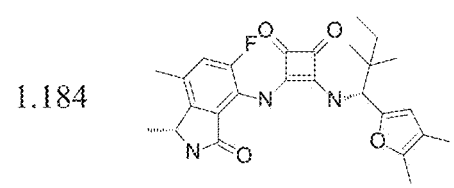
1.185 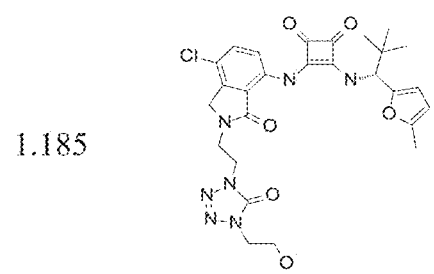
1.186 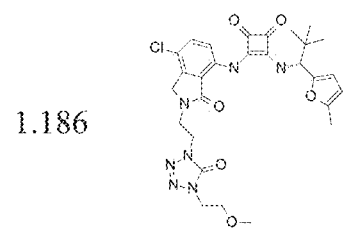
FIG. 1AJ

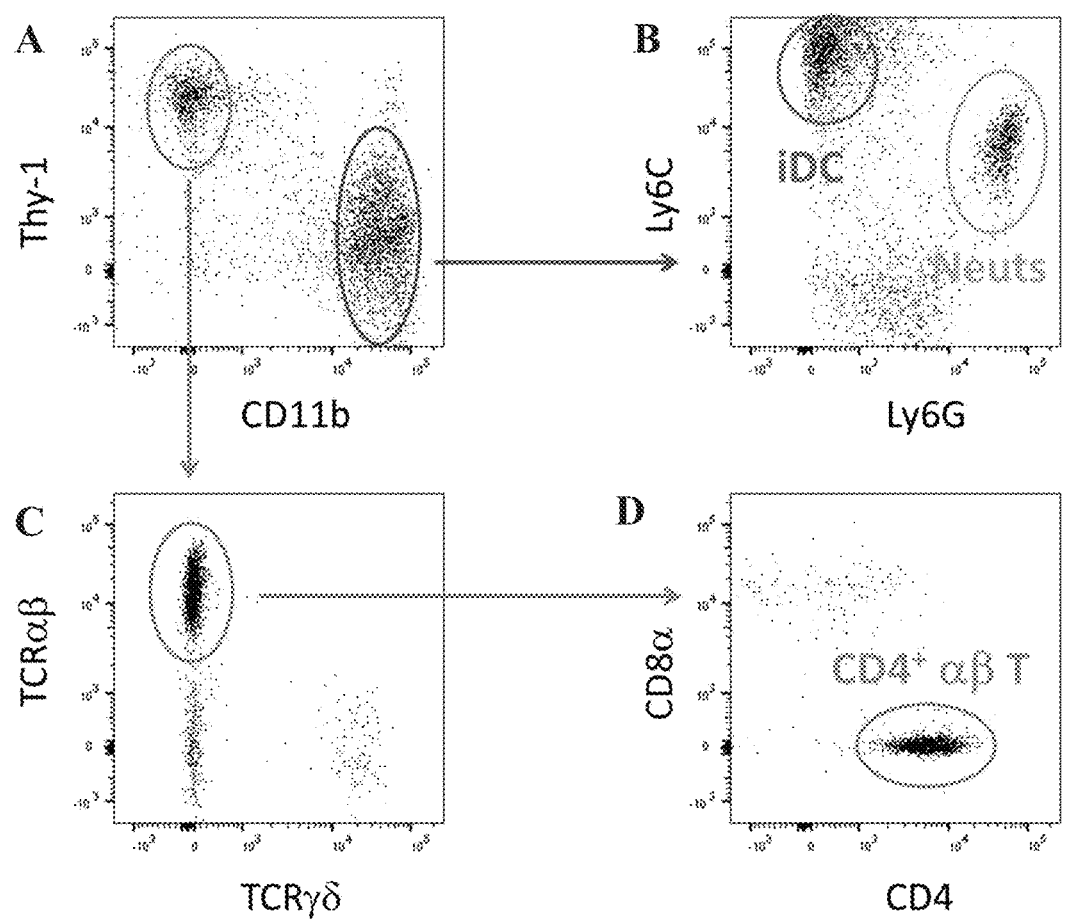
FIG. 2A-D

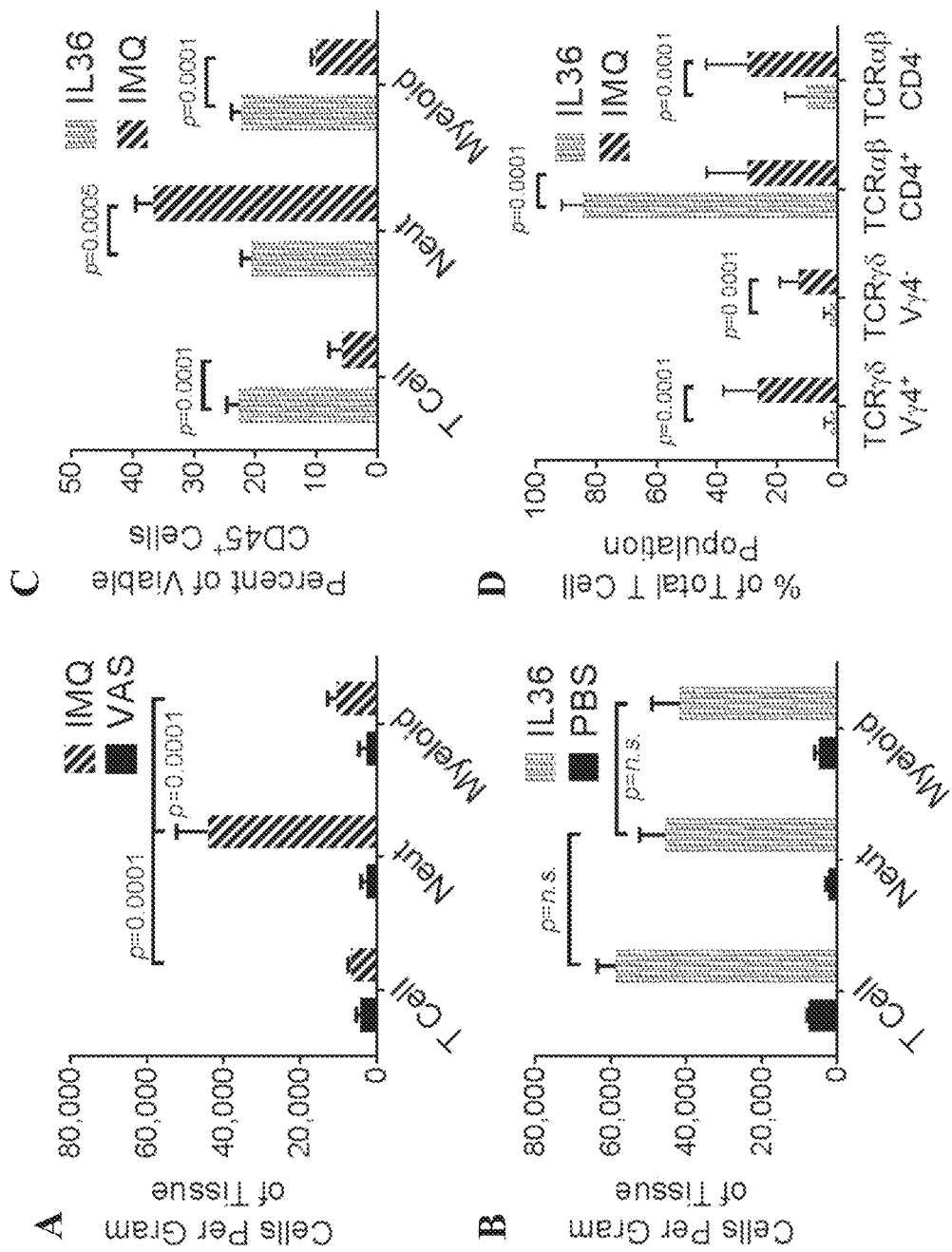
FIG. 3A-D

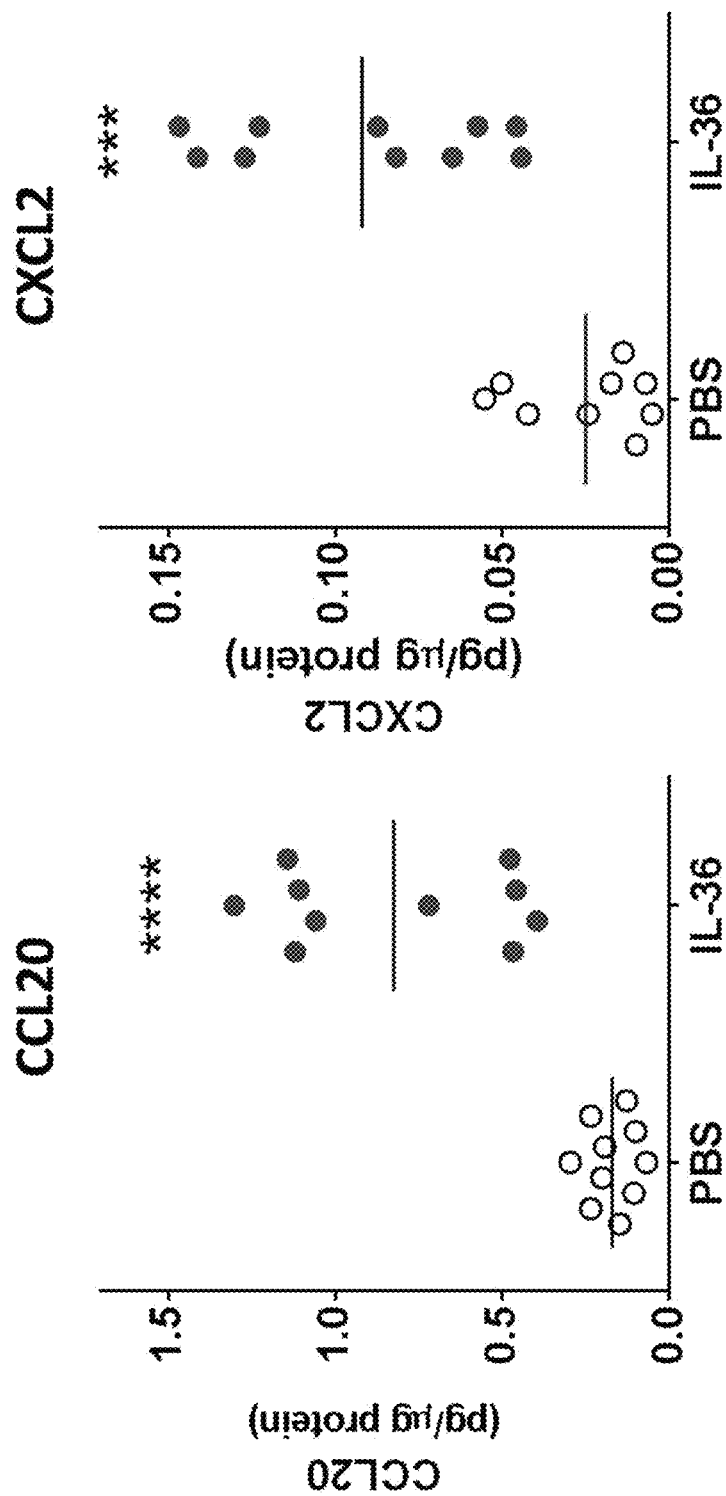
FIG. 4A-B

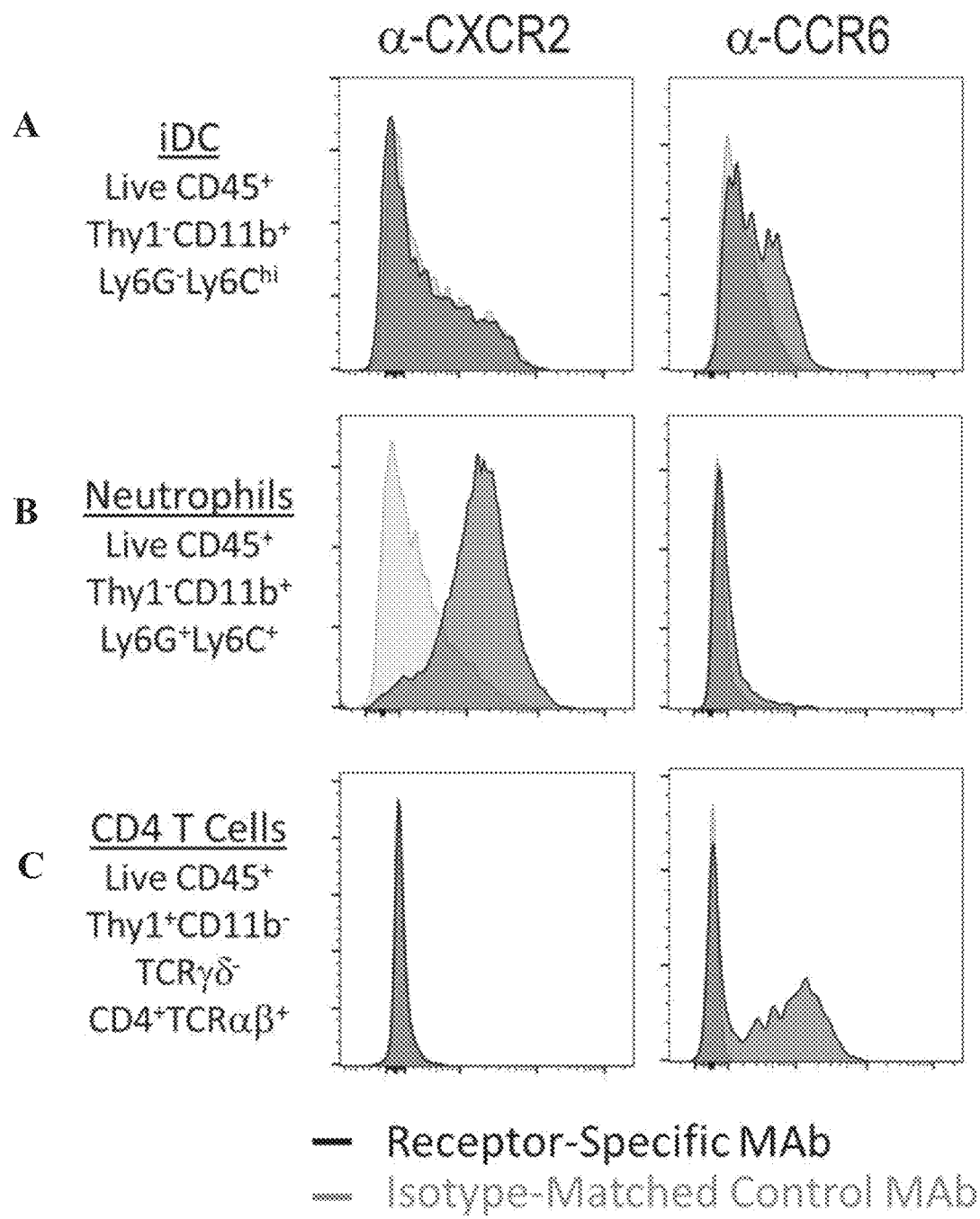
FIG. 5A-C

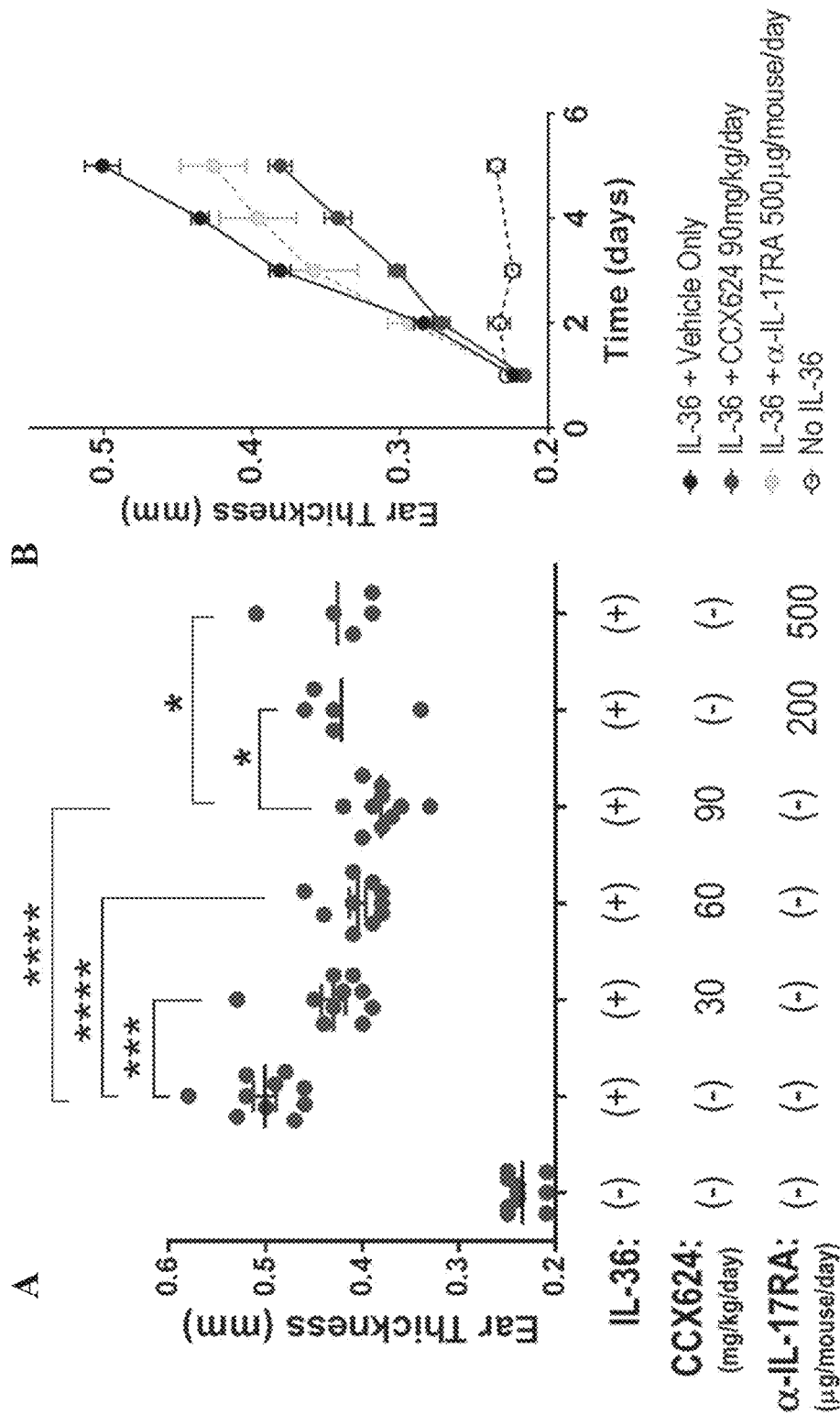
FIG. 6A-B

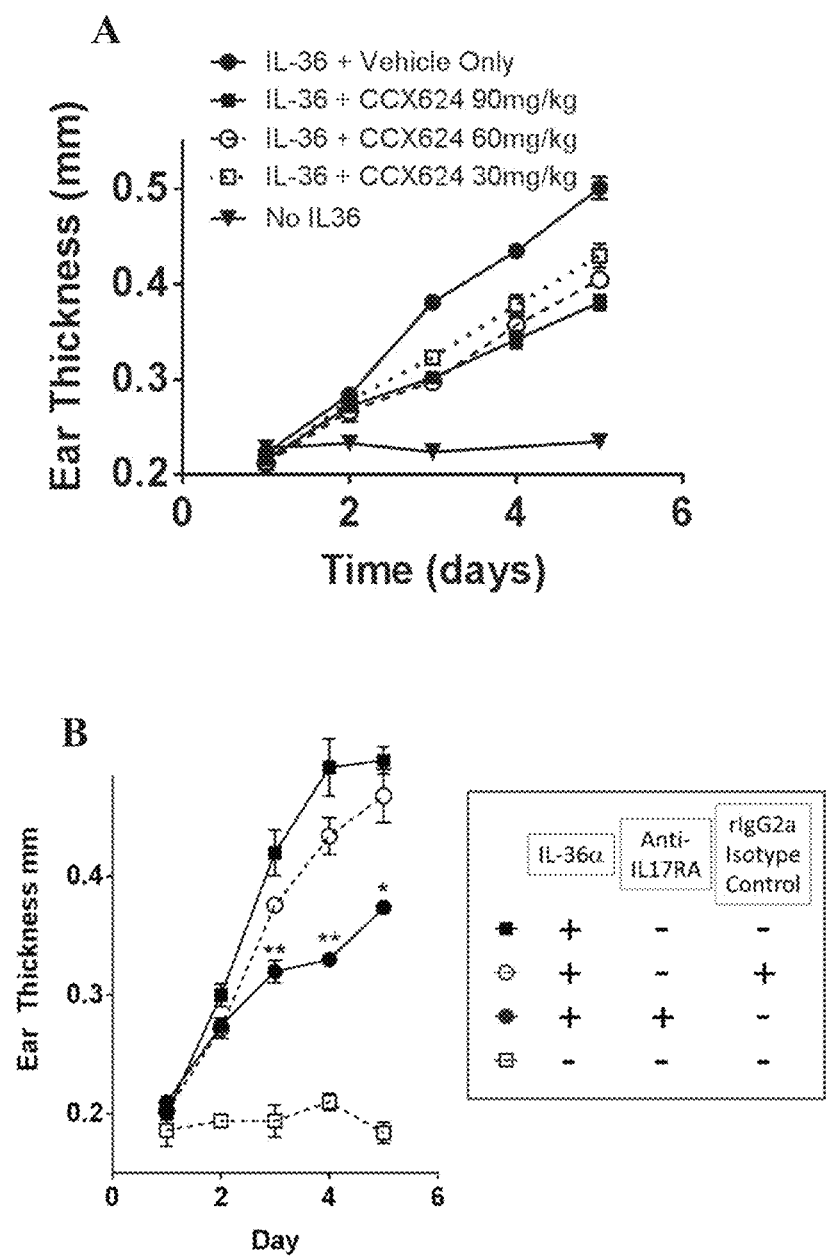
FIG. 7A-B

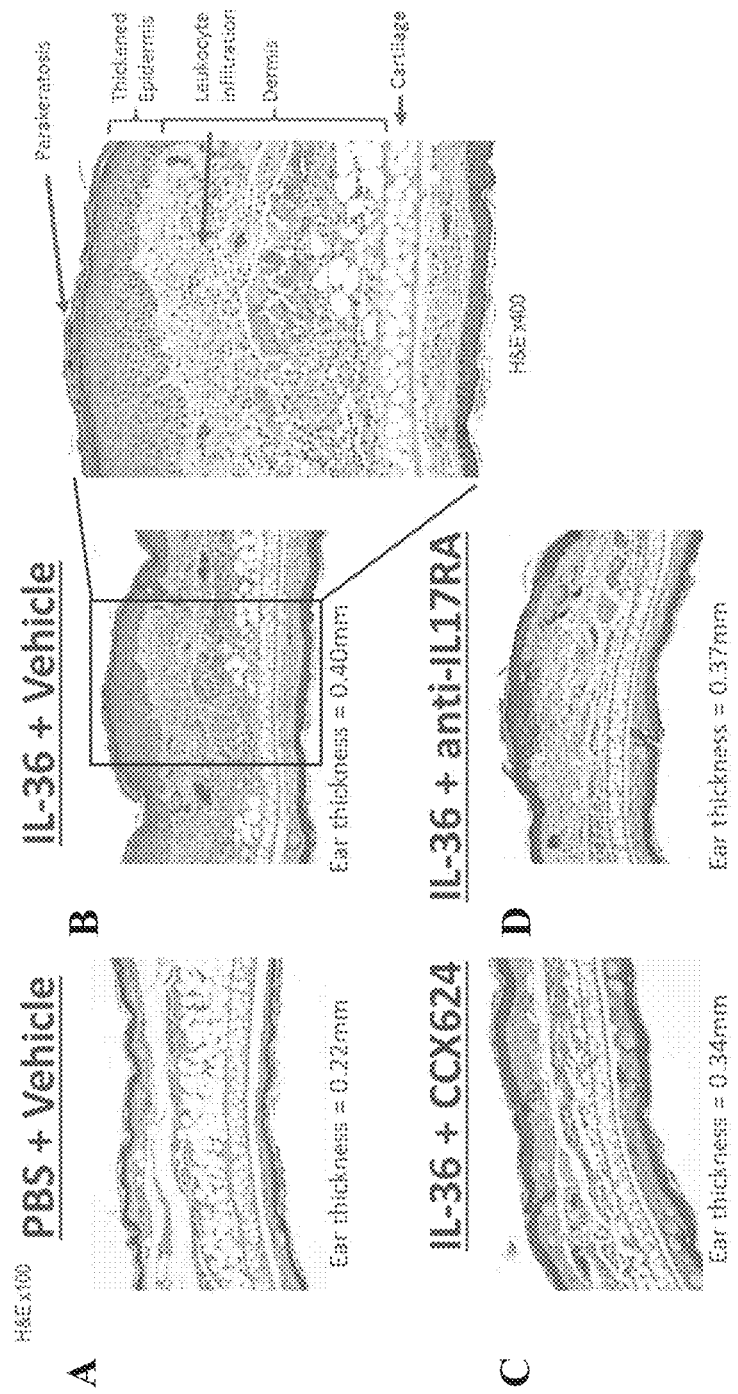
FIG. 8A-D

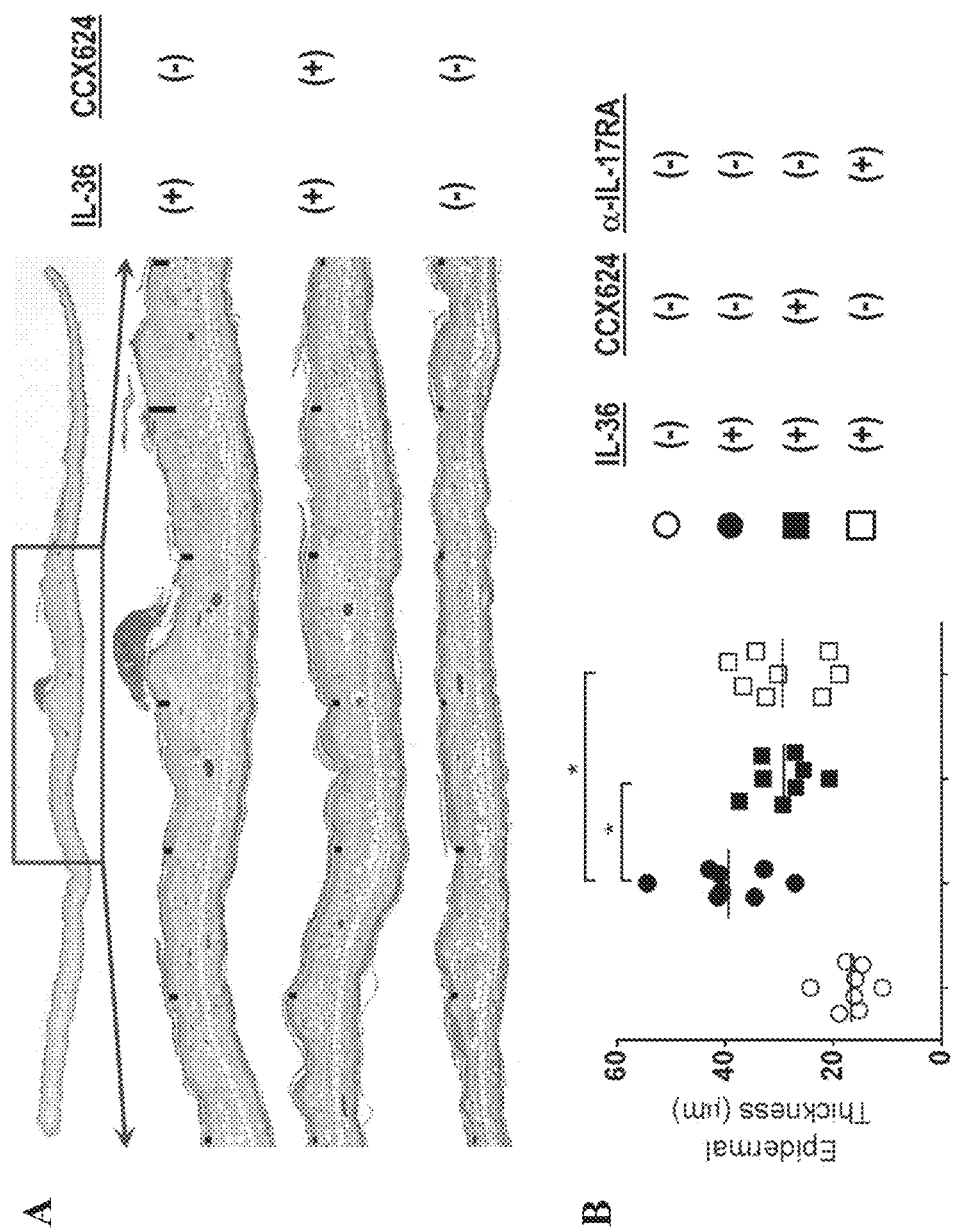
FIG. 9A-B

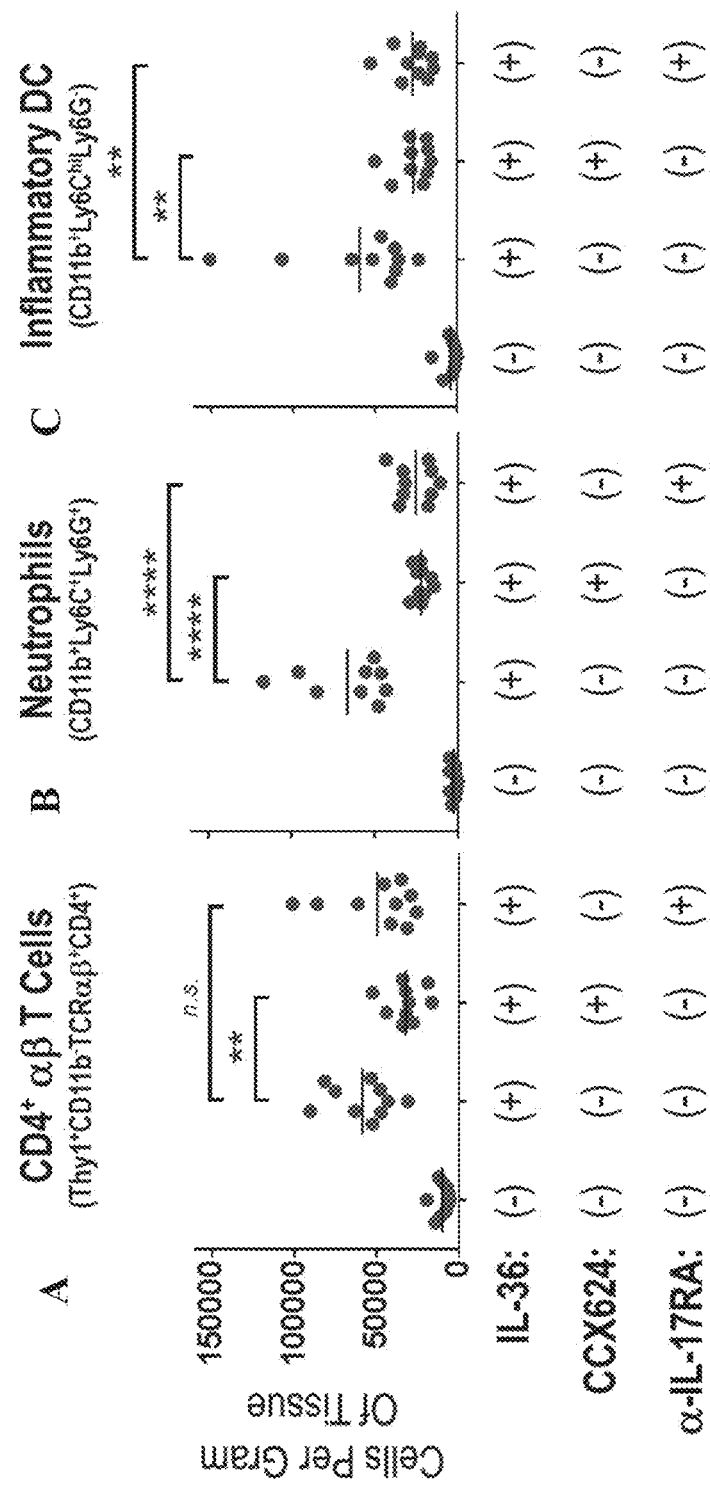
FIG. 10A-C

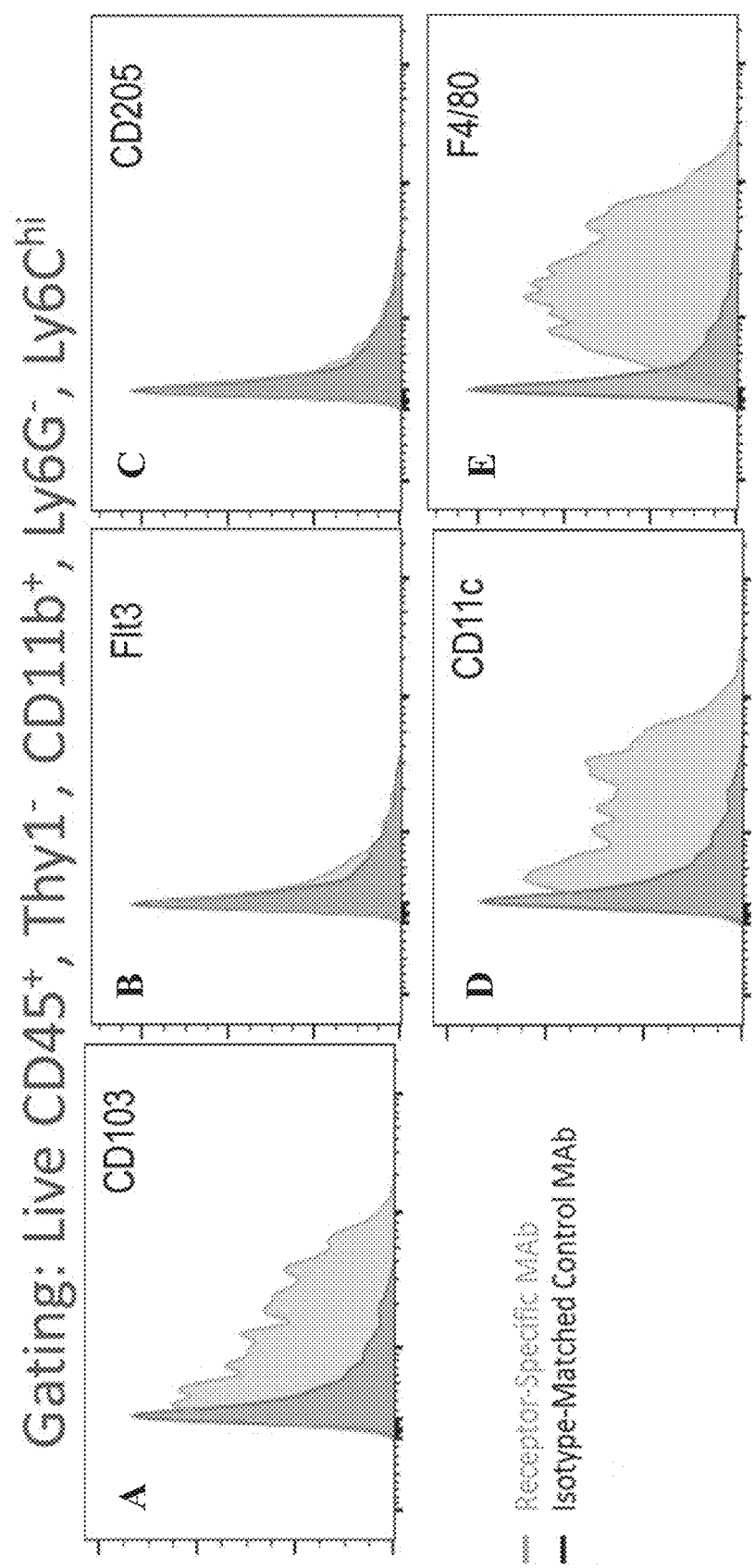
FIG. 11A-E

METHODS OF TREATING GENERALIZED PUSTULAR PSORIASIS WITH AN ANTAGONIST OF CCR6 OR CXCR2

CROSS-REFERENCES TO RELATED APPLICATIONS

This application claims the benefit of priority under 35 U.S.C § 119(e) to U.S. Provisional Application Ser. No. 62/614,927 filed Jan. 8, 2018 and U.S, Provisional Application Ser. No. 62/715,503 filed Aug. 7, 2018, the disclosure of each are incorporated herein by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND

Generalized pustular psoriasis (GPP) is a rare disease for which there is a dearth of clinical research and no universally accepted evidence-based guidelines for its treatment and management (Benjegerdes et al. *Psoriasis (Auckl)* 2016; 6:131-44.). Biologic therapies that are effective in the more common plaque form of psoriasis are ineffective in GPP (Benjegerdes of al. *Psoriasis (Auckl)* 2016; 6:131-44. Mansouri et al. *Expert Opin Biol Ther* 2013; 13(12):1715-30.), and much needed treatments that directly target GPP have not been developed (Mahil et al, *Semin Immunopathol* 2016; 38(1):11-27. Navarini et al. *J Eur Acad Dermatol Venereol* 2017; 31(11):1792-9. Robinson et al. *J Am Acad Dermatol* 2012; 67(2):279-88.

The present disclosure addresses the need for promising therapies that target and ameliorate GPP symptoms and provides related advantages as well.

BRIEF SUMMARY OF THE INVENTION

The present disclosure provides methods of treating generalized pustular psoriasis (GPP), palmo-plantar psoriasis (PPP), acute generalized exanthematous pustulosis (AGEP), hydradenitis suppurativa (HS), dermatitis herpetiformis, and/or pemphigus vulgaris said method comprising administering an effective amount of an antagonist of Chemokine Receptor 6 (CCR6) and/or C—X—C motif chemokine receptor 2 (CXCR2).

In another aspect, provided herein are methods of modulating dysregulated IL-36 signaling in a subject in need thereof, said method comprising administering to the subject an effective amount of an antagonist of Chemokine Receptor 6 (CCR6) and/or C—X—C motif chemokine receptor 2 (CXCR2).

In a further aspect, provided herein are methods of reducing neutrophil, inflammatory dendritic cell (iDC), and/or CD4 T cell accumulation in a subject in need thereof comprising administering to the subject an effective amount of an antagonist of Chemokine Receptor 6 (CCR6) and/or C—X—C motif chemokine receptor 2 (CXCR2).

In some embodiments, the CCR6 and/or CXCR2 antagonist has the formula:

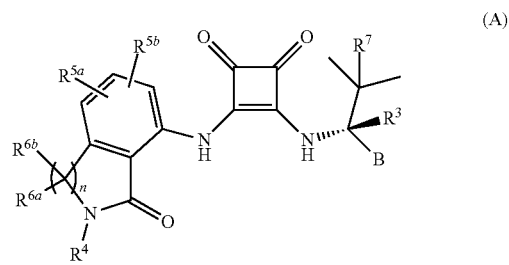

(A)

where each variable is described below.

In some embodiments, the CCR6 and/or CXCR2 antagonist has the formula:

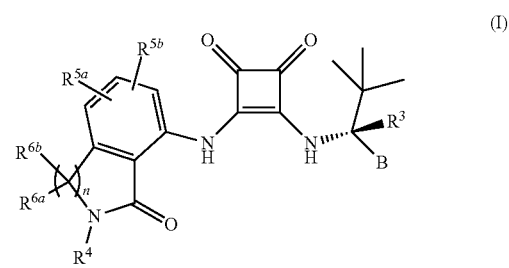

(I)

where each variable is described below.

In some embodiments, the CCR6 and/or CXCR2 antagonist is a compound shown in FIG. 1.

In some embodiments, the CCR6 and/or CXCR2 antagonist is compound 1.129:

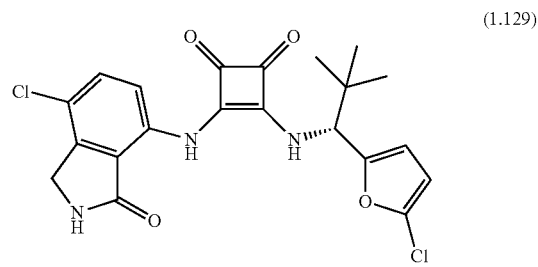 [SMILES: CC(C)(C)[C@@H](Nc1c(Nc2ccc(Cl)c3c2C(=O)NC3)c(=O)c1=O)c1ccc(Cl)o1]

(1.129)

or a pharmaceutically acceptable salt thereof.

In some embodiments, the CCR6 and/or CXCR2 antagonist is compound 1.123:

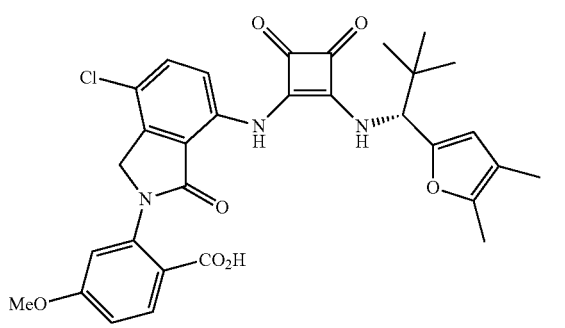

(1.123)

or a pharmaceutically acceptable salt thereof.

In some embodiments, the CCR6 and/or CXCR2 antagonist is compound 1.136:

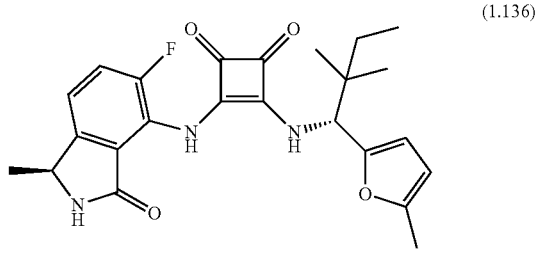 [SMILES: CCC(C)(C)[C@@H](Nc1c(Nc2c(F)ccc3c2C(=O)N[C@H]3C)c(=O)c1=O)c1ccc(C)o1]

(1.136)

or a pharmaceutically acceptable salt thereof.

In some embodiments, the CCR6 and/or CXCR2 antagonist is compound 1.138:

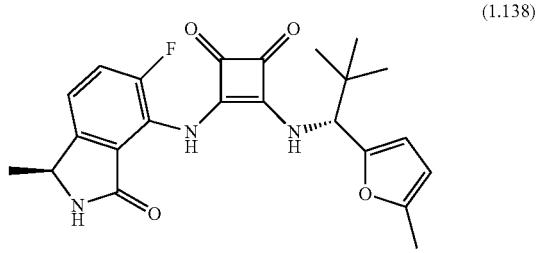 [SMILES: Cc1ccc([C@H](Nc2c(Nc3c(F)ccc4c3C(=O)N[C@H]4C)c(=O)c2=O)C(C)(C)C)o1]

(1.138)

or a pharmaceutically acceptable salt thereof.

BRIEF DESCRIPTION OF THE DRAWINGS

FIG. 2A-D shows the gating scheme used to identify iDC, neutrophils and CD4$^+$ αβ T cells isolated from IL-36-treated skin as discussed in FIG. 3, FIG. 5, and FIG. 10. The cells were first gated on the Live, CD45$^+$ population, followed by the Thy-1 vs CD11b gating (panel A). The cells circled in the lower left corner were gated on Ly6C vs Ly6G to identify iDCs and neutrophils (Panel B). The circled cells in the upper left corner of panel A were then gated on TCRαβ vs TCRγδ (Panel C). The cells circulated in panel C were gated on CD8α vs CD4 to identify CD4$^+$ αβ T cells (Panel D).

FIG. 3A-D shows the markedly different inflammatory cell skin infiltrates generated in the Imiquimod model of Plaque Psoriasis and the IL-36 Model of GPP. Panels A and B show the number of cells per gram isolated from mouse skin after four daily treatments with IMQ (A, grey bars with horizontal stripes) or IL-36α (B, grey bars with diagonal stripes). Black bars indicate the number of cells per gram isolated from control-treated skin, topical Vaseline (VAS) for the imiquimod experiments (A) and intradermal PBS for the IL-36 experiments (B). Panel C displays relative representation of leukocyte subsets within IL-36-treated versus imiquimod-treated skin: comparison among individual experiments. The percentage of T cells, neutrophils and iDC was calculated for the total live CD45$^+$ infiltrate for 5 individual imiquimod experiments and 7 individual IL-36 experiments, each experiment utilizing at least 5 individual mice. The mean of the means (and SEM) for these experiments is shown, Panel D shows that percent of T cells that expressed the indicated immunophenotype isolated from the skin of mice after treatment with imiquimod (grey bars with horizontal stripes) or IL-36α (grey bars with diagonal stripes). Each bar indicates the mean and SEM of ten mice from a single experiment, representative of at least 5 repeats. All populations shown were first gated as live (AQUA-live/dead negative) and CD45$^+$. For panels a and b, T cells were gated as Thy-1$^+$/CD11b$^-$ cells expressing either TCRβ or TCRγδ. Ly6G$^+$ and Ly6C$^{hi}$/Ly6G$^-$ cells were gated within the Thy-1$^-$/CD11b$^+$ population. For panel c, each of the indicated populations was calculated as percent of the total Thy-1$^+$/CD11b$^-$ population expressing either TCRβ or TCRγδ.

FIG. 4A-B shows multiplex analysis of CCL20 and CXCL2 proteins demonstrates significant increase of both proteins after 4 daily intradermal injections of IL-36α. CCL20 protein levels are plotted in panel A; CXCL2 protein levels are plotted in panel B.

FIG. 5A-C shows expression of CCR6 and CXCR2 by leukocytes accumulating in skin in response to intradermal IL-36α injections. Cells isolated from IL-36-treated ears of 20 mice were pooled and stained with unconjugated specific MAb (as indicated above each column) or isotype-matched control, followed by second stage MAb using standard procedures. Unbound second stage was blocked with normal mouse, rat and hamster serum, followed by directly labeled monoclonal antibodies. Gating for each cell type is indicated to the left of each row: Myeloid cells are panel A; Neutrophils are panel B; and CD4 T Cells are panel C. Percent of cells brighter than the isotype-matched control is indicated within the flow cytometry plot if greater than 5%. Staining of pooled cells is representative of 4 repeat experiments.

FIG. 6A-B shows that Compound 1.136 ameliorates inflammatory swelling of IL-36α-injected ears. Panel A plots ear thickness of mice dosed daily with Compound 1.136 at the indicated doses (or with α-IL-17RA) during the IL36α-induced GPP model. Ear thickness was measured by caliper after 4 days of treatment. Panel B Time course of ear thickness for the experiment shown in (A), comparing the 90 mg/kg dose of compound 1.136 to α-IL-17RA. Ten mice per data point. Statistics from Mann-Whitney rank order test. Note: titration experiments showed the effects of α-IL-17RA to plateau at 200 µg per mouse per day, and the mice in this experiment were dosed at 500 µg, per mouse per day (data not shown). n.s., not significant p<05*, p<0005*, p0001**.

FIG. 7A-B shows ear thickness data. Panel A shows a time course for titration of Compound 1.136 shown in FIG. 6A. Panel B shows isotype-matched control for anti-IL-17RA treatment of IL-36α-inflamed skin. Ears of five mice in each group were inflamed by daily intradermal injections of PBS or activated IL-36α as described in the text. Some groups also received daily intraperitoneal injections of 500 µg/mouse of anti-IL-17RA or 500 µg/mouse of a rat IgG2a isotype-matched negative control for the anti-IL-17RA MAb. The Mann-Whitney Rank Order test established significance between the effects of anti-IL-17RA MAb and its isotype matched control on days 3, 4 and 5. *p<0.05, **p<0.01. Although the effects of anti-IL17RA reached saturation at the 200 µg/mouse/day dose (compare to 500 µg/mouse/day in FIG. 3), anti-IL-17RA is compared to its isotype-matched control at 500 mg/kg/day to demonstrate that effects were not non-specific effects of the isotype even at these very high levels.

FIG. 8A-D shows that Compound 1.136 substantially improves histology of IL-36α-injected ears. Ears were acquired from sacrificed mice after 4 days of 90 mg/kg IL-36α or PBS treatment (Panel A is PBS+Vehicle; Panel. 13 is IL-36+Vehicle). During treatment, mice were dosed daily with 1% HPMC (the vehicle for Compound 1.136; Panels A & B), with Compound 1.136 in vehicle (Panel C) or with anti-IL17RA (Panel D). Ears were fixed and embedded using standard FFPE techniques, sectioned and stained using standard hematoxylin and eosin (H&E) staining techniques. Sections shown are representative of at least five different sections from five different ears.

FIG. 9A-B shows that Compound 1.136 substantially reduces epidermal thickness of ears injected with activated IL-36α. Panel A, top row shows a section of an entire width of ear after 4 daily IL-36α injections. Panel A, second row shows a higher magnification of the top image focusing on the lesional area. Panel A, rows three and four show lesional areas from Compound 1.136-treated IL-36α-treated mouse ear and mouse ear injected with PBS instead of IL-36α. Black bars indicate where the each of the 7 individual epidermal thickness measurements were taken for all sections graphed in Panel B. Panel B, ear thickness measurements from 8 mice from each treatment group. Each dot represents the mean of 7 epidermal thickness measurements from the ear of 1 mouse. Ears were acquired from sacrificed mice after 4 daily treatments of activated IL-36α (or PBS). During treatment, mice were dosed daily subcutaneously with 1% HPMC (the vehicle) with Compound 1.136 at 90 mg/kg/day s.c. in vehicle, or with anti-IL17RA at 200 µg/mouse/day IP in PBS. Ears were fixed and embedded using standard FFPE techniques, sectioned and stained using standard hematoxylin and eosin (H&E) staining techniques. Sections shown are representative of at least five different sections from eight different ears. Statistics from Mann-Whitney rank order test p<05*.

FIG. 10A-C shows that Compound 1.136 significantly reduces accumulation of CD4 T cells (Panel A), neutrophils (Panel B), and inflammatory dendritic cells (Panel C) within IL-36-treated skin. Ears were acquired from sacrificed mice after 4 daily IL-36α (or PBS control) treatments. IL-36α-injected mice received vehicle alone, Compound 1.136 (90 mg/kg/day s.c. on the back) or α-IL-17RA (200 µg/mouse/day in the peritoneum). Statistical analysis by Mann-Whitney rank-order test. One experiment is shown with 10 mice per group and is representative of 3 repeats. n.s., not significant, p<005, p<0001**.

DETAILED DESCRIPTION OF TILE INVENTION

General

Figure 1A:
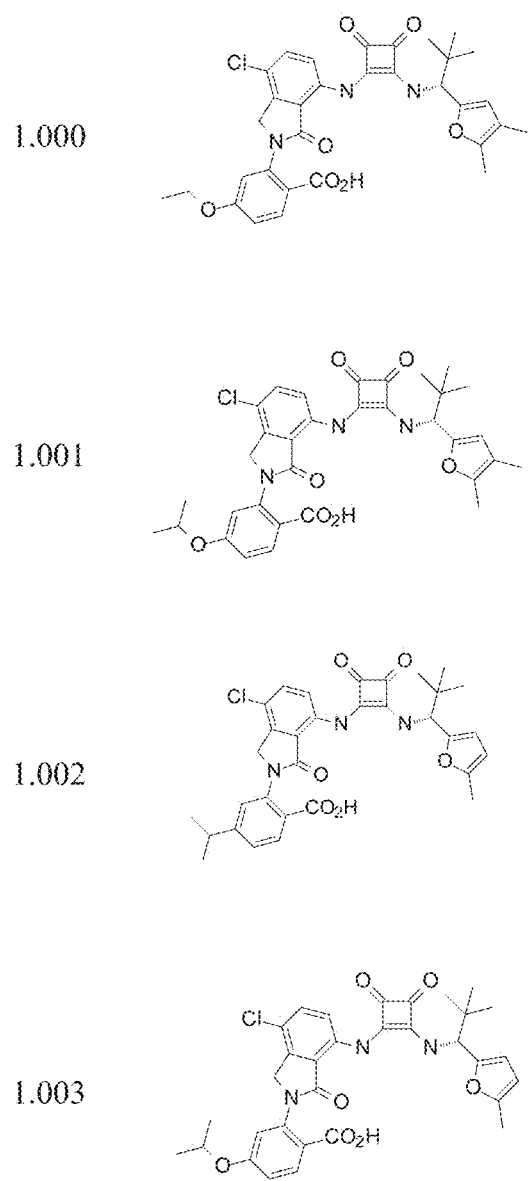
FIG. 1A-1AJ provides particular structures for compounds described herein.

Generalized pustular psoriasis (GPP) is a rare inflammatory skin disorder with an etiology distinct from the more common plaque psoriasis. GPP patients often do not respond to therapeutic agents typically used for plaque psoriasis. Antagonists of CCR6 and/or CXCR2 including the compounds disclosed herein have been previously shown to ameliorate inflammation in a model of plaque psoriasis. Surprisingly, the present disclosure demonstrates that an antagonist of CCR6 and/or CXCR2 can be used to effectively treat generalized pustular psoriasis (GPP). In addition to treating GPP, related diseases such as palmo-plantar psoriasis (PPP), acute generalized exanthematous pustulosis (AGEP), hydradenitis suppurativa (HS), dermatitis herpetiformis, and pemphigus vulgaris can also be treated using the methods described herein.

Chemokine directed therapy is designed to block the migration of inflammatory leukocytes into tissues from the peripheral blood, thus preventing them from participating in and amplifying any existing autoimmune lesions, thereby allowing the inflammatory cytokine environment to dissipate. Genetic studies demonstrate that GPP is strongly associated with dysfunctions in the IL-36 cytokine axis, and many aspects of GPP can be re-created in the mouse by intradermal injection of pre-activated IL-36αcytokine. The present disclosure demonstrates that the immune cells infiltrating IL-36α-injected mouse skin are of dramatically different composition than those infiltrating imiquimod—(IMQ-) treated skin, an accepted model of plaque psoriasis in Balb/c mice. The findings disclosed herein suggest that CCR6 and CXCR2 antagonists may constitute a novel target class for a mechanistically distinct therapeutic approach to treat GPP as well as related PPP, AGEP, HS, dermatitis herpetiformis, and pemphigus vulgaris diseases.

Abbreviations and Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, a wavy line, "⌇", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse) For example, the group "—(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$haloalkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted C$_{1-8}$ alkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)—NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_{1-4}$)alkoxy, and perfluoro(C$_{1-4}$) alkyl, in a number ranging from zero to the total number of open valences on the aromatic ring system; and where R', R" and R'" are independently selected from hydrogen, C$_{1-8}$alkyl, C$_{1-8}$haloalkyl C$_{3-6}$ cycloalkyl, C$_{2-8}$ alkenyl and C$_{2-8}$ alkynyl. Other suitable substituents include each of the above aryl substituents attached to a ring atom by an alkylene tether of from 1-4 carbon atoms, Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—,—NH—, —S—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N) sulfur (S) and silicon (Si).

When a variable (e.g., R$^1$ or R$^a$) occurs more than one time in any compound or substituent, its definition on each occurrence is independent of its definition at every other occurrence. Additionally, combinations of substituents and/or variables are permissible only if such combinations result in stable compounds.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an antagonist of CCR6 and/or CXCR2, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", "treatment" and the like refer to a course of action (such as administering an antagonist of CCR6 and/or CXCR2, or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an antagonist of CCR6 and/or CXCR2, or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an antagonist of CCR6 and/or CXCR2 (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy, indicators include any objective parameter (e.g., serum concentration) or subjective parameter (e.g., a subject's feeling of well-being).

The term "small molecules" refers to chemical compounds having a molecular weight that is less than about 10 kDa, less than about 2kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of CCR6 and/or CXGR2, either directly or indirectly. A modulator may act alone, or it may use a cofactor, e.g., a protein, metal ion, or small molecule.

The "activity" of a molecule may describe or refer to the binding of the molecule o a receptor; to catalytic activity; to the ability to stimulate gene expression or cell signaling, differentiation, or maturation; to antigenic activity; to the modulation of activities of other molecules; and the like.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total content of the composition. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

DETAILED DESCRIPTION OF EMBODIMENTS

Methods of Use

Provided herein are methods of using antagonist of Chemokine Receptor 6 (CCR6) and/or C—X—C motif chemokine receptor 2 (CXCR2.) to prevent, reduce, or maintain leukocyte accumulation (such as neutrophil, inflammatory dendritic cell (iDC), and/or CD4 T cell accumulation), manage and modulate diseases related to IL-36 dysregulation, and the treatment of diseases such as generalized pustular psoriasis (GPP), palma-plantar psoriasis (PPP), acute generalized exanthematous pustulosis AGEP), hydradenitis suppurativa (HS), dermatitis herpetiformis, and pemphigus vulgaris. As described herein, the present disclosure demonstrates that antagonist of Chemokine Receptor 6 (CCR6) and/or C—X—C motif chemokine receptor 2 (CXCR2) effectively modulates leukocyte migration typically observed in subjects experiencing IL-36 dysregulation. Administration of a Chemokine Receptor 6 (CCR6) and/or C—X—C motif chemokine receptor 2 (CXCR2) effectively ameliorates inflammation in these subjects.

As such, in one aspect, the present disclosure provides methods of treating a disease or condition selected from generalized pustular psoriasis (GPP), palmo-plantar psoriasis (PPP), acute generalized exanthematous pustulosis (AGEP), hydradenitis suppurativa (HS), dermatitis herpetiformis, or pemphigus vulgaris, said method comprising administering an effective amount of an antagonist of Chemokine Receptor 6 (CCR6) and/or C—X—C motif chemokine receptor 2 (CXCR2).

In some embodiments, the disease or condition is generalized pustular psoriasis (GPP). In some embodiments, the disease or condition is palmo-plantar psoriasis (PPP). In some embodiments, the disease or condition is acute generalized exanthematous pustulosis (AGEP). In some embodiments, the disease or condition is hydradenitis suppurativa (HS). In some embodiments, the disease or condition is dermatitis herpetiformis. In some embodiments, the disease or condition is pemphigus vulgaris.

In another aspect, provided herein are methods of modulating dysregulated IL-36 signaling in a subject in need thereof, said method comprising administering to the subject an effective amount of an antagonist of Chemokine Receptor 6 (CCR6) and/or C—X—C motif chemokine receptor 2 (CXCR2).

In a further aspect, provided herein are methods of reducing neutrophil, inflammatory dendritic cell (iDC), and/or CD4 T cell accumulation in a subject in need thereof comprising administering to the subject an effective amount of an antagonist of Chemokine Receptor 6 (CCR6) and/or C—X—C motif chemokine receptor 2 (CXCR2).

Antagonists of CCR6 and/or CXCR2

In some embodiments, the CCR6 and/or CXCR2 antagonist has the formula:

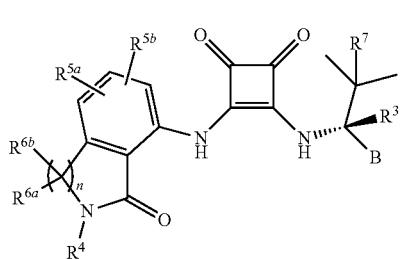

(A)

wherein
B is selected from the group consisting of furanyl, thiophenyl, oxazolyl, phenyl, pyridyl, pyrimidinyl and pyrazinyl, each of which is optionally substituted with $R^{1a}$, $R^{1b}$, and $R^2$ which are independently selected from the group consisting of halogen, CN, $C_{1-4}$ alkyl, $C_{1-4}$ alkoxy and $C_{1-4}$ haloalkyl;

$R^3$ is a member selected from the group consisting of H and D;

$R^4$ is a member selected from the group consisting of H, $C_{1-8}$ alkyl, OH, —$NR^aR^b$, —$C_{1-4}$ alkoxy, and Y; wherein the $C_{1-8}$ alkyl is optionally substituted with halogen, —CN, —$CO_2R^a$, —$CONR^aR^b$, —$C(O)R^a$, $OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$ and Y, wherein Y is a 4 to 8 membered cycloheteroalkyl group or a 3 to 8 membered cycloalkyl group or a 5- or 6-membered aryl or heteroaryl group any of which is optionally substituted with from 1 to four substituents selected from halogen, oxo, —CN, —$C_{1-6}$ alkyl, —$C_{1-6}$ alkoxy, —$C_{1-6}$ hydroxyalkyl, —$C_{1-6}$ haloalkyl, O—$C_{1-6}$ haloalkyl, —$C_{1-4}$alkyl-O—$C_{1-4}$ alkyl, —$C_{1-6}$ alkyl- $NR^aR^b$, —$C_{1-6}$ alkyl-$CO_2H$, —$C_{1-6}$ alkyl-$CO_2R^a$, —$C_{1-6}$ alkyl-$CONR^aR^b$, —$C_{1-6}$ alkyl-$C(O)R^a$, —$C_{1-6}$ alkyl-OC(O) $NR^aR^b$, —$C_{1-6}$ alkyl-$NR^aC(O)R^b$, —$C_{1-6}$ alkyl-$NR^aC(O)_2R^c$, —$C_{1-6}$ alkyl-$NR^aC(O)NR^aR^b$, —$C_{1-6}$ alkyl-$OR^a$, —$C_{1-6}$ alkyl-$S(O)_2NR^aR^b$, —$C_{1-6}$ alkyl-$NR^aS(O)_2R^b$, —$CO_2R^a$, —$CONR^aR^b$, —$C(O)R^a$, —$OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$, —$CH_2CO_2R^a$; each $R^a$ and $R^b$ is independently selected from hydrogen, $C_{1-4}$ alkyl, $C_{1-4}$ hydroxyalkyl and $C_{1-4}$ haloalkyl, and $R^c$ is selected from $C_{1-4}$ alkyl, $C_{1-4}$ hydroxyalkyl and $C_{1-4}$ haloalkyl; and wherein the 4 to 8 membered cycloheteroalkyl group and the 3 to 8 membered cycloalkyl group may additionally be optionally substituted with oxo;

$R^{5a}$ and $R^{5b}$ are each members independently selected from the group consisting of H, halogen, $C_{1-4}$ alkyl, —$C_{1-4}$ haloalkyl, O—$C_{1-4}$ haloalkyl, $C_{1-4}$ alkoxy, $CO_2H$ and CN;

$R^{6a}$ and $R^{6b}$ are each members independently selected from the group consisting of H, $C_{1-4}$ alkyl, $C_{1-4}$ hydroxyalkyl and $C_{1-4}$ haloalkyl; or optionally $R^{6a}$ and $R^{6b}$ are taken together to form oxo (=O) or a 4 to 6 membered cycloheteroalkyl group or a 3 to 6 membered cycloalkyl group;

$R^7$ is a member selected from the group consisting of methyl, ethyl and $C_{1-2}$ haloalkyl; and the subscript n is 1 or 2;

or any pharmaceutically acceptable salts, solvates, hydrates, N-oxides, tautomers or rotamers thereof.

In some embodiments, the CCR6 and/or CXCR2 antagonist has the formula:

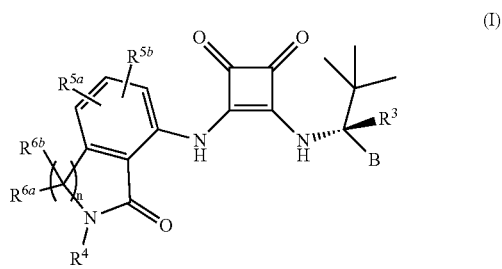

(I)

or any salts, solvates, hydrates, N-oxides, tautomers or rotamers thereof, wherein B is selected from the group consisting of furanyl, oxazolyl, phenyl, pyridyl, pyrimidinyl and pyrazinyl, each of which is optionally substituted with $R^{1a}$, $R^{1b}$, and $R^2$ which are independently selected from the group consisting of halogen, CN, $C_{1-4}$ alkyl, $C_{1-4}$ alkoxy and $C_{1-4}$ haloalkyl;

$R^3$ is a member selected from and $R^4$ is a member selected from H, $C_{1-8}$ alkyl, and Y; wherein the $C_{1-8}$ alkyl is optionally substituted with halogen, —CN, —$CO_2R^a$, —$CONR^aR^b$, —$C(O)R^a$, $OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$ and Y, wherein each $R^a$ and $R^b$ is independently selected from hydrogen, $C_{1-4}$ alkyl, $C_{1-4}$ hydroxyalkyl and $C_{1-4}$ haloalkyl, $R^c$ is selected from $C_{1-4}$ alkyl, $C_{1-4}$ hydroxyalkyl and $C_{1-4}$ haloalkyl, and Y is a 5 or 6 membered aryl or heteroaryl group optionally substituted with from one to four substituents selected from halogen, —CN, —$C_{1-4}$ alkyl, —$C_{1-4}$ alkoxy, —$C_{1-4}$ hydroxyalkyl, —$C_{1-4}$ haloalkyl, $OCF_3$, —$CO_2R^a$, —$CONR^aR^b$, —$C(O)R^a$, —$OC(O)NR^aR^b$, —$NR^aC(O)R^b$, —$CH_2CO_2R^a$;

$R^{5a}$ and $R^{5b}$ are each members independently selected from H, halogen, $C_{1-4}$ alkyl $C_{1-4}$ alkoxy, $CO_2H$ and CN;

$R^{6a}$ and $R^{6b}$ are each members independently selected from H, $C_{1-4}$alkyl, $C_{1-4}$ hydroxyalkyl and $C_{1-4}$ haloalkyl; or optionally $R^{6a}$ and $R^{6b}$ are taken together to form oxo (=O); and the subscript n is 1 or 2.

In some embodiments, the CCR6 and/or CXCR2 antagonist has the formula:

(A1)

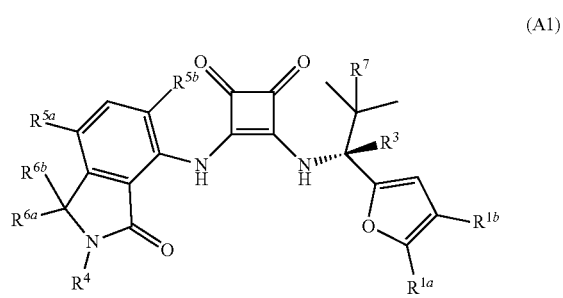

wherein $R^{1a}$ is selected from $CH_3$ and Cl; $R^{1b}$ is H or is $CH_3$; $R^3$ is H or D; $R^4$ is H or Y; $R^{5a}$ and $R^{5b}$ are each independently selected from H., F, Cl, Br and $CH_3$; $R^{6a}$ and $R^{6b}$ are each independently selected from H and $CH_3$; and $R^7$ is methyl or ethyl; or a pharmaceutically acceptable salt, solvate or hydrate, thereof.

In some embodiments, $R^{1a}$ is $CH_3$; $R^{1b}$ is absent or is $CH_3$; $R^3$ is H or D; $R^4$ is H; $R^{5a}$ is H, F, Me or Cl or Br; $R^{5b}$ is H or F; $R^{6a}$ and $R^{6b}$ are each H; and $R^7$ is methyl or ethyl; or a pharmaceutically acceptable salt, solvate or hydrate, thereof.

In some embodiments, the compound is substantially free of other isomers at the carbon atom bearing $R^3$.

In some embodiments, $R^4$ is Y.

In some embodiments, a compound of formula (A2) is provided:

(A2)

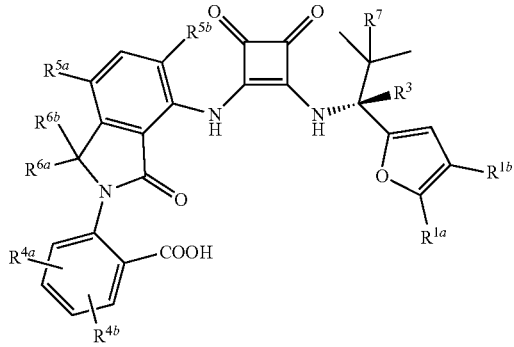

wherein $R^{1a}$ is selected from $CH_3$ and Cl; $R^{1b}$ is H or $CH_3$; $R^3$ is H or D; $R^{4a}$ and $R^{4b}$ are independently selected from halogen, —CN, —$C_{1-4}$ alkyl, —$C_{1-4}$ alkoxy, $C_{1-4}$ hydroxyalkyl, —$C_{1-4}$ haloalkyl, $OCF_3$, —$CO_2R^a$, —$CONR^aR^b$, —$C(O)R^a$, —$OC(O)NR^aR^b$, —$NR^aC(O)R^b$, —$CH_2CO_2R^a$, and $R^a$and $R^b$ are independently selected from hydrogen, $C_{1-4}$ alkyl, $C_{1-4}$ hydroxyalkyl and $C_{1-4}$ haloalkyl; $R^{5a}$ and $R^{5b}$ are each independently selected from H, F, Cl, Br and $CH_3$; $R^{6a}$ and $R^{6b}$ are each independently selected from H and $CH_3$; and $R^7$ is selected from the group consisting of methyl, ethyl and $C_{1-2}$ haloalkyl; or a pharmaceutically acceptable salt, solvate or hydrate, thereof.

In some embodiments, a compound, or a pharmaceutically acceptable salt thereof, is provided, selected from the group consisting of:

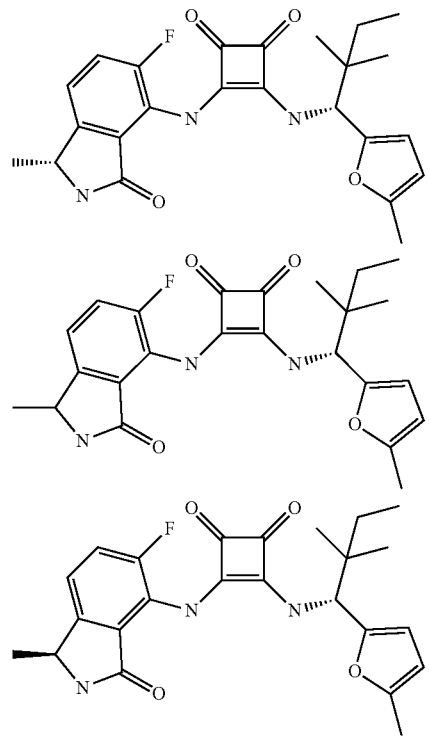

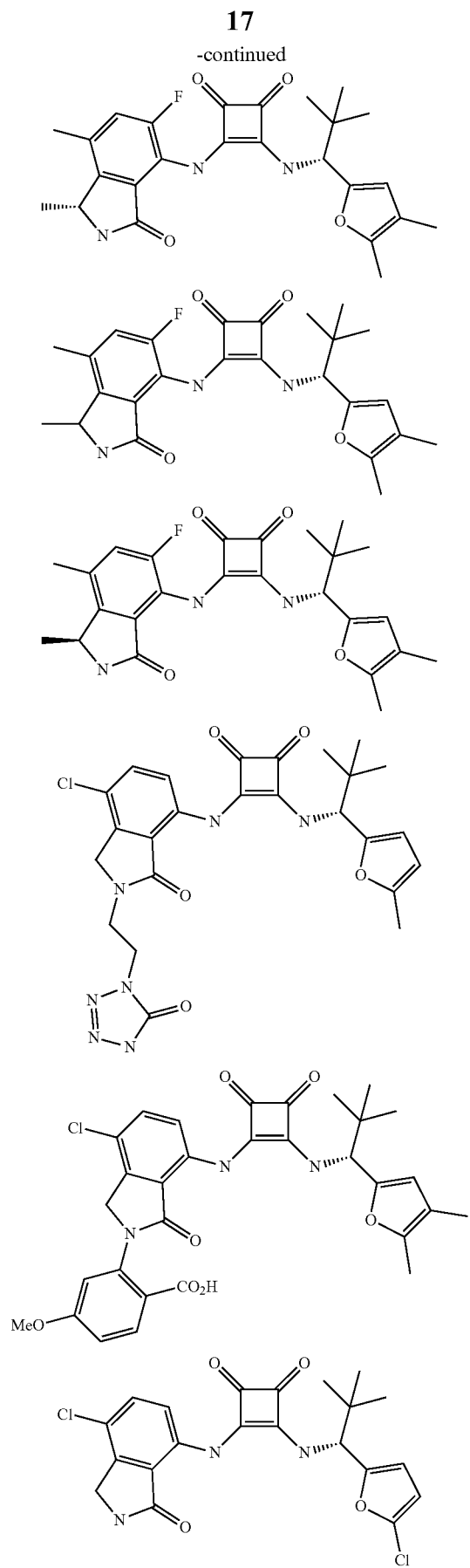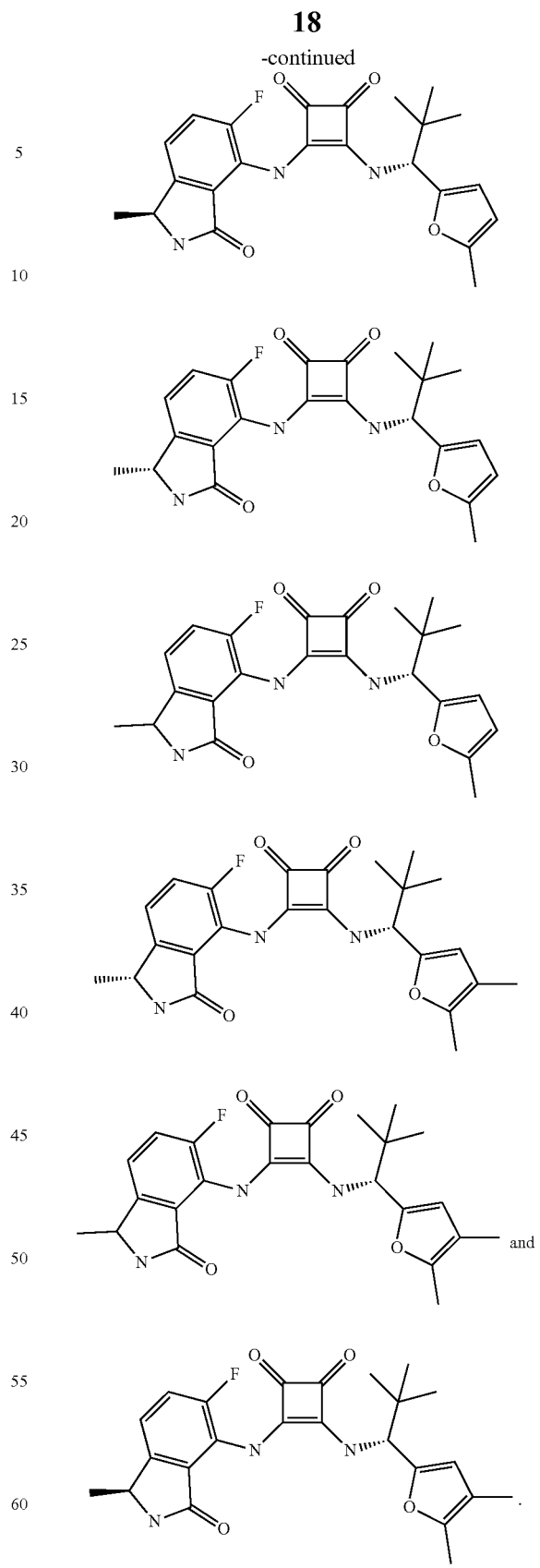
In some embodiments, a compound, or a pharmaceutically acceptable salt thereof, is provided, selected from the group consisting of:

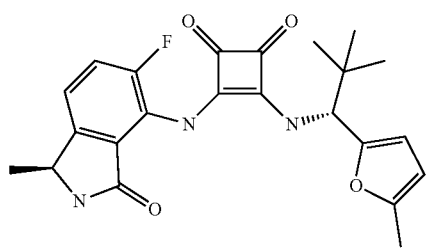
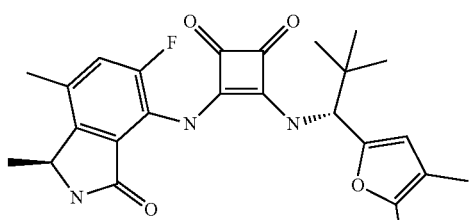
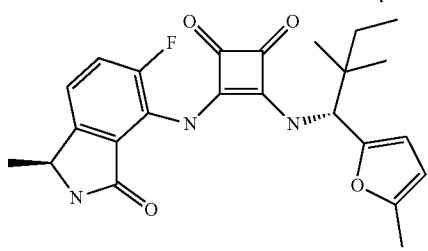
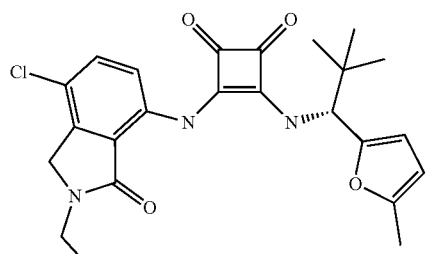
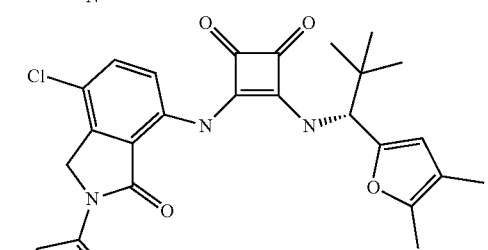
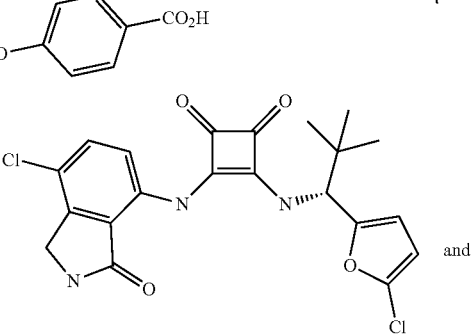
and
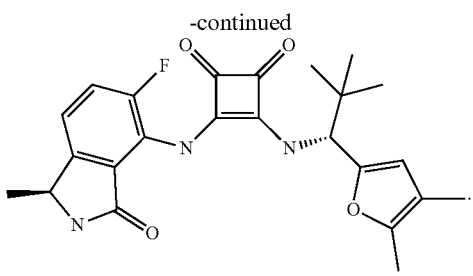
-continued
In some embodiments, a compound, or a pharmaceutically acceptable salt thereof, is provided, selected from the group consisting of:
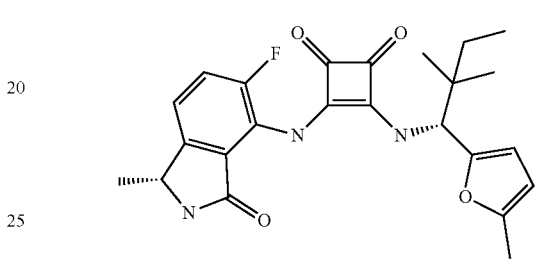
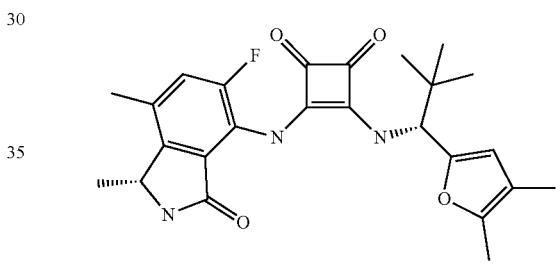
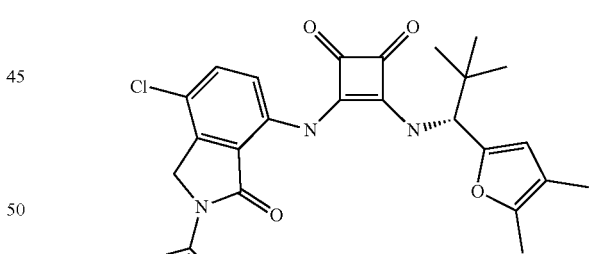
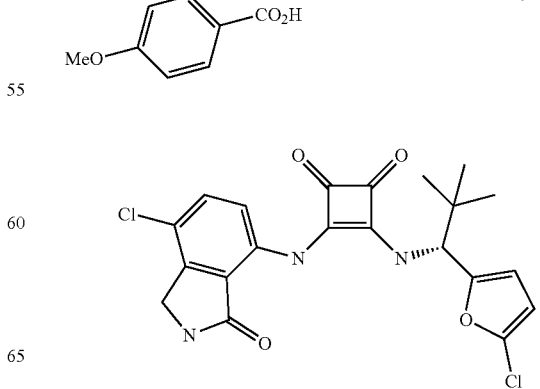

-continued

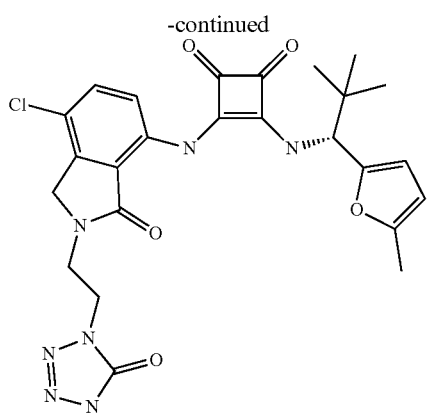

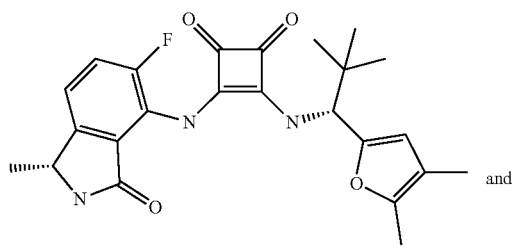
and

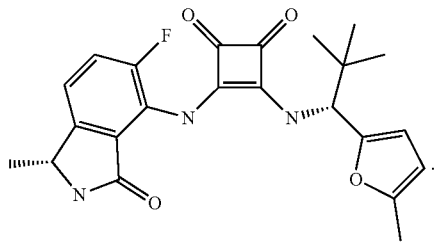.

In some selected embodiments, compounds of formula e provided that are selected from those compounds in FIG. 1.

In some embodiments, the CCR6 and/or CXCR2 antagonist is compound 1.129:

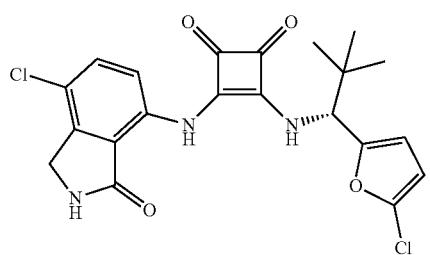
(1.129)

or a pharmaceutically acceptable salt thereof.

In some embodiments, the CCR6 and/or CXCR2 antagonist is compound 1.123:

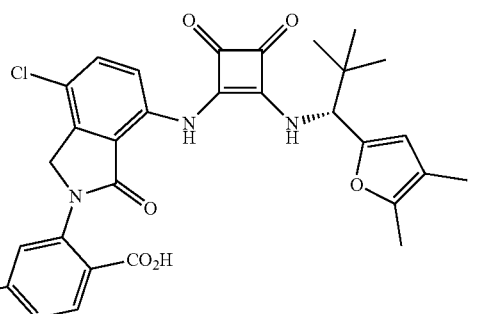
(1.123)

or a pharmaceutically acceptable salt thereof.

In some embodiments, the CCR6 and/or CXCR2 antagonist is compound 1.136:

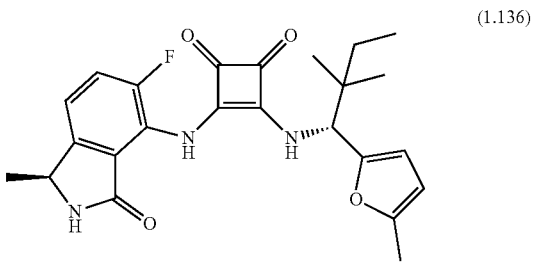 [SMILES: CCC(C)(C)[C@@H](Nc1c(Nc2c(F)ccc3c2C(=O)N[C@H]3C)c(=O)c1=O)c1ccc(C)o1]
(1.136)

or a pharmaceutically acceptable salt thereof.

In some embodiments, the CCR6 and/or GXCR2 antagonist is compound 1.138:

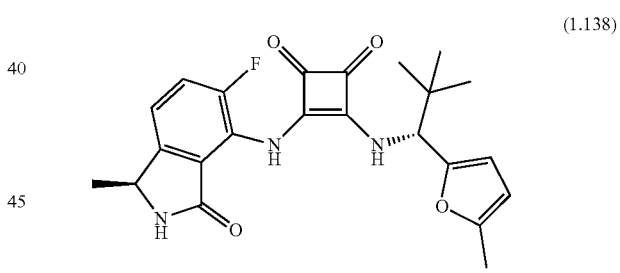
(1.138)

or a pharmaceutically acceptable salt thereof.

In some embodiments, the CCR6 and/or CXCR2 antagonist is selected from the compounds or pharmaceutical compositions disclosed in U.S. Pat. No. 9,834,545, stemming from application Ser. No. 15/353,889, filed on Nov. 17, 2016 by ChemoCentryx, the content of which is incorporated herein for all purposes.

Pharmaceutical Compositions

In addition the compounds described above, the compositions for modulating CCR6 and/or CXCR2 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, flavoring and/or coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.' and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PULA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with paltnitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S, Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

In some embodiments, a pharmaceutical composition comprising a compound of the present disclosure is provided. In some embodiments, the pharmaceutical composition further comprises one or more additional therapeutic agents. In some embodiments, the one or more additional therapeutic agent is selected from the group consisting of cytotoxic chemotherapy, anti-cancer or anti-tumor vaccines, anti-immunocytokine therapies, immunocytokine therapies, chimeric antigen receptor (CAR) T cell receptors, gene transfer therapy, checkpoint inhibitors, corticosteroids, retinoid-like agents, antineoplastics, and interferons analogs. In some embodiments, the one or more additional therapeutic agent is selected from the group consisting of a TNF alpha ligand inhibitor, a TNF binding agent, an IL-1 ligand inhibitor; an IL-6 ligand inhibitor, an IL-8 ligand inhibitor; an IL-17 antagonist, a calcineurin inhibitor, a TNF antagonist, a Retinoic acid receptor gamma antagonist, an IL-17A ligand inhibitor; an IL-17F ligand inhibitor, a RIP-1 kinase inhibitor, a sphingosine-1-phosphate receptor-1 antagonist, a sphingosine-1-phosphate receptor-1 modulator, a Rho associated protein kinase 2 inhibitor, an IL-12 antagonist; an IL-23 antagonist, a type II TNF receptor modulator, an IL-23A inhibitor, a PDE 4 inhibitor, a JAK tyrosine kinase inhibitor, a Jak1 tyrosine kinase inhibitor; a Jak3 tyrosine kinase inhibitor, a Histamine H1 receptor antagonist, a Retinoic acid receptor agonist, a membrane copper amine oxidase inhibitor, a PI3K modulator, a Phosphoinositide-3 kinase delta inhibitor, a mitochondria 10 kDa heat shock protein stimulator, an adenosine A3 receptor agonist, a galectin-3 inhibitor, a F1F0 ATP synthase modulator, a GM-CSF ligand inhibitor, a vitamin D3 receptor agonist, a glucocorticoid agonist, a histamine H4 receptor antagonist, a CCR3 chemokine antagonist, an eotaxin ligand inhibitor, a Sphingosine-1-phosphate receptor-1 modulator, a phospholipase A2 inhibitor, a PDE 4 inhibitor, an albumin modulator, a TLR-7 antagonist, a TLR-8 antagonist a TLR-9 antagonist, a CD40 ligand receptor antagonist, a Src tyrosine kinase inhibitor, a tubulin binding agent, an interleukin-1 alpha ligand inhibitor, a histone deacetylase-1 inhibitor, a histone deacetylase-2 inhibitor, a histone deacetylase-3 inhibitor, a histone deacetylase-6 inhibitor, a nucleoside reverse transcriptase inhibitor, a nuclear factor kappa B inhibitor, a STAT-3 inhibitor, a parathyroid hormone ligand inhibitor; a vitamin D3 receptor agonist, a T cell surface glycoprotein CD28 stimulator, a histamine H4 receptor antagonist, a TGF beta agonist, a P-selectin glycoprotein ligand-1 stimulator, a DHFR inhibitor, a Retinoic acid receptor gamma modulator, a cytosolic phospholipase A2. inhibitor, a retinoid X receptor modulator, a beta-catenin inhibitor, a CREB binding protein inhibitor, a TrkA receptor antagonist, a T-cell differentiation antigen CD6 inhibitor, an ADP ribosyl cyclase-1 inhibitor, an Interleukin-1 beta ligand modulator; an insulin receptor substrate-1 inhibitor, a DHFR inhibitor, an IL-8 antagonist, a drug that blocks the activity of CTLA-4 (CD152), PD-1 (CD279), PDL-1 (CD274), TLM-3, LAG-3 (CD223), VISTA, KIR, NKG2A, BTLA, PD-1H, TIGIT, CD96, 4-1BB (CD137), 4-1BBL (CD137L), CARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

Methods of Administration

In general, treatment methods provided herein comprise administering to a patient an effective amount of one or more compounds provided herein. In a preferred embodiment, the compound(s) of the invention are preferably administered to a patient (e.g., a human) orally or topically. Treatment regimens may vary depending on the compound used In general, a dosage regimen of 2 times daily is more preferred, with once a day dosing particularly preferred. It will he understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner in general, the use of the minimum dose sufficient to provide effective therapy is preferred. Patients may generally be monitored for therapeutic effectiveness using medical or veterinary criteria suitable for the condition being treated or prevented.

The compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional nontoxic pharmaceutically acceptable carriers, adjuvants and vehicles appropriate for each route of administration. The present invention also contemplates administration of the compounds and compositions of the present invention in a depot formulation.

Dosage levels of the order of from about 0.1 mg to about 1100 mg per kilogram of body weight per day are useful in the treatment or preventions of conditions involving pathogenic CCR6 and/or CXCR2 activity (about 0.5 mg to about 7 g per human patient per day). Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograins)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

I EXAMPLES

Example 1

IL36-Mediated Skin Inflammation Requires Signaling Through Chemokine Receptor CCR6

Generalized pustular psoriasis (GPP) is a rare inflammatory skin disorder with an etiology distinct from the more common plaque psoriasis. GPP patients often do not respond to therapeutic agents typically used for plaque psoriasis. Genetic evidence suggests that GPP arises from dysfunctions in the IL36/IL36R$^a$/IL36R signaling axis, and many aspects of GPP can be re-created through intradermal (ID) injection of pre-activated IL36 in the mouse. We have used this ID-IL36 model to study the leukocyte populations accumulating within GPP skin. In a previous study, we reported that small molecule CCR6 antagonist Compound 1,129 ameliorates inflammation in a topical imiquimod-induced model of plaque psoriasis. CCR6 antagonism prevents accumulation of IL17-secreting γδ T (γδT17) in this model, which appears to be the mechanism by which Compound 1.129 alleviates disease. We have found in the present study that γδT17 cells do not accumulate in IL36-inflamed skin. Instead, a conventional CD4$^+$ αβ T cell population accumulates in in this model. Compound 1.129 reduces IL36-induced inflammation while preventing accumulation of this CD4$^+$ αβ T cell population. Thus, although disparate T cell populations are associated with each model, inflammation is ameliorated in both by CCR6 antagonism and CXCR2 antagonism. These findings suggest that CCR6 may constitute a novel target for a mechanistically distinct approach for GPP therapy.

Example 2

Inhibition of Chemokine Receptor and Ligand Interactions Reverses IL-36-Induced Inflammation Materials and Methods For in vitro determination of chemokine receptor inhibitor activity, Compound 1.136 was dissolved in DMSO to generate a stock concentration of 10 mM that was further diluted in chemotaxis migration buffer (HBSS, 1% BSA, 1% HEPES) to create a 10-point inhibitor gradient ranging from 100 nM-0.01 nM. Migration assay was then run in 100% mouse serum in response to rmCCL20 for CCR6 activity or rmCXCL1 for CXCR2 activity using ChemoTx plates (Neuroprobe, Gaithersburg Md.) and assessed by fluorescence staining of migrated cells with CyQuant (Thermo Fisher).

Balb/c mice were purchased from Jackson Laboratories (Bar Harbor, Me.) and housed at ChemoCentryx animal facility in accordance with guidelines described in the Guide and Use of Laboratory Animals of the National Research Council. All studies were approved by the ChemoCentryx Institutional Animal Care and Use Committee.

For in vivo dosing, mice were dosed subcutaneously with Compound 1,136 once daily (s.c, q.d. in 1% HPMC) at 90 mg/kg unless stated otherwise, starting at day 0 of a study. The in vivo dose was predicted based on in vitro potency and the pharmacokinetic response to a single dose in mice. The minimum antagonist concentration (at trough) to fully cover a gradient-sensing chemoattractant receptor has been determined to correspond with the $IC_{90}$ concentration (Schall, T. J., and A. E. Proudfoot. 2011, Overcoming hurdles in developing successful drugs targeting chemokine receptors. Nat Rev Immunol 11: 355-363). The $IC_{90}$ of Compound 1.136 in 100% serum is 45 ng/ml for CCR6 inhibition and 145 ng/ml for CXCR2 inhibition. The actual trough concentrations achieved in vivo for Compound 1.136 at 30, 60 and 90 mg/kg are shown in Table 1.

TABLE 1

Mean ± s.d. plasma concentrations measured at trough (i.e. 24 hours post final dose (day 5)) for animals dosed with 90, 60, 30 mg/kg Compound 1.136 in 1% HPM

| | Compound 1.136 Dose (mg/kg) | | |
|---|---|---|---|
| | 90 mg/kg | 60 mg/kg | 30 mg/kg |
| Compound 1.136 Trough Value (ng/ml) | 973 ± 19 | 323 ± 20 | 267 ± 18 |

Mouse model of IL-36-induced ear thickening. The right ear of 8-week old Balb/c mice received intradermal injections of recombinant murine IL-36α, (150 µg per mouse formulated in PBS; BioLegend) every day for 5 days. Intradermal injections of PBS were given to the left ear as a control. Ear thickness was measured prior to start of study and each day throughout the study using a digital micrometer. The imiquimod model of psoriasifom dermatitis was performed as previously described (Campbell J et al. J Immunol. 2017, 199(9):3129-36. van der Fits et al. J Immunol 2009, 182(9):5836-45). Briefly, 5% Imiquimod (Fougera®) was applied daily to the shaved and depilated backs of Balb/c mice for up to 4 days. Control mice were treated with an application of Vaseline. Erythema, desquamation, and skin thickening were scored independently on a scale from 0 to 4 where 0=no disease; 1=slight disease; 2=moderate disease; 3=marked disease; 4=very marked disease (Campbell J et al. *J Immunol.* 2017; 199(9):3129-36. van der Fits et al, *J Immunol* 2009; 182(9):5836-45). Skin from the backs of mice was excised at the end of the study and processed for flow cytometry analysis.

Flow cytometry of leukocytes. Ears or excised skin samples were digested in collagenase A and 1 U/ml DNAse I with agitation for 30 min at 37° C. Cells were then dislodged from skin, filtered through a 70 μM sieve, washed and re-suspended in FACS buffer (PBS with 10% FBS) for analysis.

Directly conjugated Monoclonal antibodies were from R&D Systems (Minneapolis, Minn.), BioLegend (San Diego, Calif.), or eBioscience/ThermoFisher (San Diego, Calif.). CD45.2 (104) in AlexaFluor488, Ly6C (HK1.4) in PE, CD90.2 (30-H12) in Per CP-Cy5.5, TCRVγ4 (UC3-10A6) in PE-Cy7, TCRβ (H57-597) in APC, CD4 (GK1.5) in APC-eFluor-780, TCRγδ (GL3) in BV-421, LIVE/DEAD fixable Aqua stain (Molecular Probes, Eugene, Oreg.), CD11c (N418) in BV650, Ly6G (1A4) in BV711 and CD11b (M1/70) in BV785. Flow cytometry data were acquired with a Fortessa (BD Biosciences) cytometer and analyzed using FlowJo v10.2.

Figure 11:
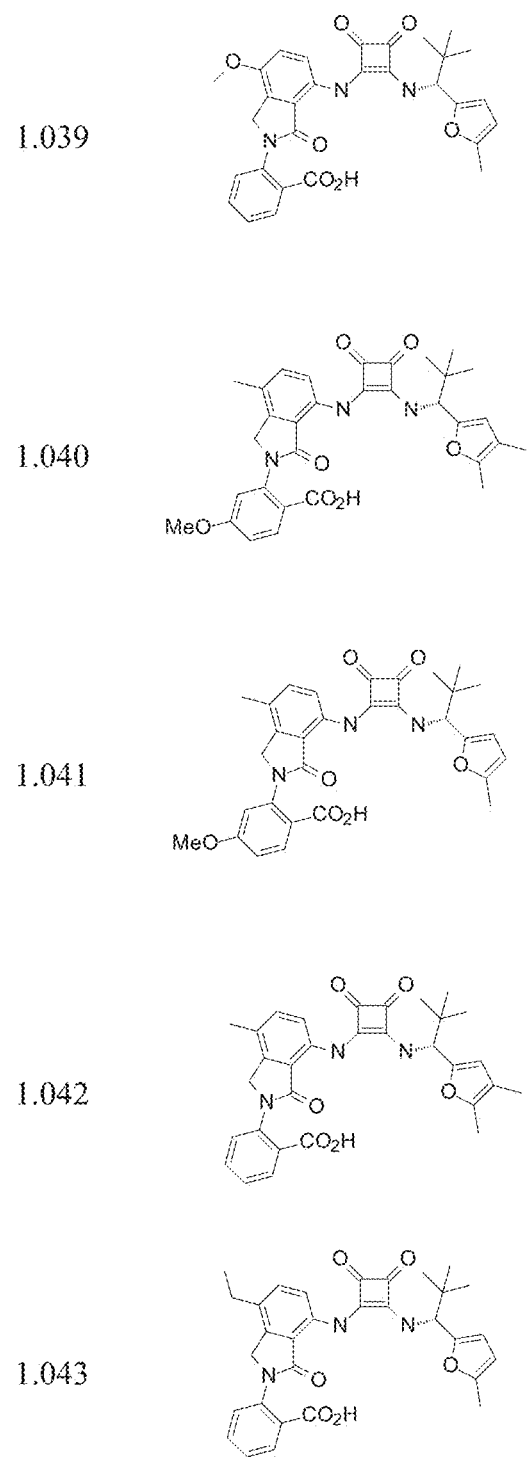
FIG. 11A-E shows the characterization of Ly6C$^{hi}$ myeloid cells accumulating in skin after intradermal IL-36α injections. Cells were isolated from 20 ears after four daily IL-36α injections, then pooled and stained with unconjugated specific MAb (as indicated within each panel, light grey curves) or isotype-matched controls (dark grey curves), followed by an anti-Ig second stage polyclonal Ab using standard procedures. Unbound second stage was blocked with normal mouse, rat and hamster serum, followed by directly conjugated MAbs. Panel A uses a CD103 specific MAb; Panel B uses a Flt3 specific MAb; Panel C uses a CD205 specific MAb; Panel D uses a CD11c specific MAb; and Panel E uses a F4/80 specific MAb. Myeloid cells were gated as in FIG. 5A. Staining of pooled cells shown is representative of 3 repeat experiments.

Flow cytometry of leukocytes extracted from inflamed skin shown in FIG. 5 and FIG. 11 involved a panel of unconjugated monoclonals (or their isotype-matched controls) followed by an appropriate APC-conjugated polyclonal (FAB)$_2$ (Jackson ImmunoResearch, West Grove, Pa., USA). These unconjugated reagents included anti-CCR6 (140706) from R&D Systems (Minneapolis, Minn.). and anti-CXCR2 (SA044G4) from Biolegend (San Diego, Calif.) all rat IgG2as. Unconjugated MAbs against lineage markers CD103, CD11c, FLT3, CD205, and F4/80 were all obtained from Biolegend. After staining with unconjugated monoclonal and APC polyclonal, the cells were blocked with 10% mouse, 10% hamster and 10% rat sera (Jackson ImmunoResearch) prior to staining with direct conjugates.

Mouse anti-IL,17RA. (R&D Systems) was dosed as a positive control at 200-500 μg per mouse, i.p., q.d. The 200 μg/ml per mouse per day dosing was found to be well within the plateau of maximal activity for this treatment (FIG. 6A).

Multiplex analysis of chemokine protein concentration in skin. Ear tissue collected after 4 days of intradermal IL-36α treatments was homogenized in cold PBS containing protease inhibitors (Roche) then centrifuged to remove debris. The soluble fraction was assayed using a multiplex assay kit according to manufacturers instructions (R&D systems) and read on a MagPix (Luminex) analyzer. The concentration of tissue chemokines was normalized against the total protein levels measured for each sample using the standard Bradford assay.

For hematoxylin and eosin (H&E) staining, ear tissue was initially fixed in paraformaldehyde for paraffin embedding. Samples were processed by standard procedures. Epidermal thickness was measured as the average of 7 measurements made along the center third (the area containing the lesion) of the length of the H&E stained ear sections using Photoshop CS4 software (Adobe®)

Statistical significance was determined by Mann Whitney calculation using GraphPad Prism 6.0 software.

Results & Discussion

Inflammatory cell populations were compared within inflamed skin obtained from two murine models of psoriasis. For plaque psoriasis, the well-established imiquimod (IMQ) model was used (van der Fits et al. *J Immunol* 2009; 182(9):5836-45), in which the TLR 7/8 agonist IMQ is applied daily to the surface of depilated skin. For GPP, daily intra-cutaneous injections of activated mouse IL-36α to the ear was used.

After 4 days of treatment flow cytometry showed inflammatory cell infiltrates isolated from skin (Gated as shown in FIG. 2) differ appreciably between the two models. IMQ treatment generated a large neutrophil population (FIG. 3A & FIG. 3C) whereas activated IL-36α generated nearly equal numbers of T cells, neutrophils and Ly6C$^{hi}$/Ly6G$^-$ myeloid cells (FIG. 3B & FIG. 3C). The T cell populations from each model were also highly divergent FIG. 3D); IMQ-treated skin (grey bars with horizontal stripes) having a prominent γδT17 (Vγ4$^+$) population (as previously observed (Cai et al. *Immunity* 2011; 35(4):596-610. Campbell J et al. *J Immunol.* 2017; 199(9):3129-36.)), and T cells from IL-36α-injected skin (grey bars with diagonal stripes) consisted almost entirely of CD4$^+$ "conventional" αβ T cells.

The myeloid skin population induced by IL-36 expressed a combination of markers characteristic of both myeloid and dendritic cells (FIG. 11). These cells expressed CD103, CD11c and F4/80. They did not express Flt3, a marker diagnostic of classical dendritic cells (cDC), nor did they express CD205 (DEC205) (FIG. 11). Based on this immunophenotype, and the location of these cells within actively inflamed skin, we believe these cells to be monocyte-derived inflammatory dendritic cells (iDC) (Merad et al. *Annu Rev Immunol* 2013; 31:563-604.) and will refer to them as such for this point on.

We observed that chemokine ligands for CCL20 and CXCR2 were significantly increased in skin by treatment with IL-36α (FIG. 4), in agreement with previous work. (Campbell, J. J., K. Ebsworth, L. S. Ertl, J. P. McMahon, D. Newland, Y. Wang, S. Liu, Z. Miao, T. Dang, P. Zhang, I. F. Charo, R. Singh, and T. J. Schall. 2017. IL-17-Secreting gammadelta. T Cells Are Completely Dependent upon CCR6 for Homing to Inflamed Skin, *j Immunol* 199: 3129-3136 & van der Fits, L., S. Mourits, J. S. Voerman, M. Kant, L Boon, J. D. Laman, F. Cornelissen, A. M. Mus, E. Florencia. Prens, and E. Lubberts. 2009. Imiquimod-induced psoriasis-like skin inflammation in mice is mediated via the IL-23/1L-17 axis. *J Immunol* 182: 5836-5845.) We used flow cytometry to examine CCR6 and CXCR2 expression on each of the three leukocyte subtypes comprising most of the CD45+ infiltrate that accumulated in response to IL-36 (FIG. 5). Of these three, only neutrophils expressed CXCR2 levels greater than isotype control staining (FIG. 5B, left column). A minority of the iDC and a majority of CD4 T cells expressed CCR6 (FIG. 5A, right column).

The prominence of CCR6 and CXCR2 ligand in the inflamed skin coupled with the expression of these two receptors by the IL-36α-induced subsets prompted us to assess a CCR6/CXCR2 antagonist for efficacy in preventing these cells from accumulating within the skin (and thereby ameliorating IL-36α-induced skin inflammation). Compound 1.136 is a small molecule with a molecular weight of ~440 and an IC$_{50}$ of 10 nM on mouse CCR6 and 20 nM on mouse CXCR2 as assessed by in vitro inhibition of chemotaxis in 100% serum. The table below provides further information on Compound 1.136 in vitro inhibition.

TABLE 2

In vitro Activity of Compound 1.136

| | CC and CXC Chemokine Receptors | | | | | | | | |
|---|---|---|---|---|---|---|---|---|---|
| Compound | mCCR6 [a] | mCXCR2 [b] | mCCR1 [c] | mCCR2 [d] | mCCR4 [e] | mCCR5 [f] | mCCR7 [g] | mCCR9 [h] | mCXCR4 [i] |
| 1.136 | 10 | 20 | >10,000 | >10,000 | >10,000 | >10,000 | 6,000 | >10,000 | >10,000 |

[a] $IC_{50}$ for chemotaxis of mCCR6-transfected BaF3 cells to mCCL20 in serum.
[b] $IC_{50}$ for chemotaxis of mouse bone marrow cells to mCXCL1 in plasma.
[c] $IC_{50}$ for chemotaxis of mouse WEHI-274.1 cells to mCCL3 in serum.
[d] $IC_{50}$ for chemotaxis of mouse bone marrow cells to mCCL2 in serum.
[e] $A_2$ for chemotaxis of mCCR4-transfected BaF3 cells to mCCL22 in serum.
[f] $IC_{50}$ for chemotaxis of mCCR5-transfected BaF3 cells to mCCL5 in serum.
[g] $IC_{50}$ for chemotaxis of mouse splenocytes to mCCL19 in serum.
[h] $IC_{50}$ for chemotaxis of mouse thymocytes to mCCL25 in serum.
[i] $IC_{50}$ for chemotaxis of mouse BaF3-WT to mCXCL12 in serum.

We measured ear thickness after 4 daily intradermal injections of PBS alone (negative control) or activated IL-36α in PBS (FIG. 6). The mean thickness of PBS-treated ears was ~2.5 mm, half as thick as the IL-36α-treated ears (~5.0mm, FIG. 6A). Compound 1.136 was subcutaneously dosed once daily (on the back of the mouse, distal from the IL-36-treated ear), and achieved dose-dependent decreases in IL-36-induced ear thickening (FIG. 6A). A time course revealed that the effects of Compound 1.136 were appreciable after the second day of treatment (FIG. 613 and FIG. 7A).

We next compared the effectiveness of Compound 1.136 to that of an α-IL-17RA monoclonal antibody (200 or 500 μg per mouse dosed IP once daily). Anti-IL-17RA treatment was effective at reducing IL-36-induced ear swelling (FIG. 6A), but was significantly less effective than the 90 mg/kg dose of Compound 1.136. The separation in effectiveness between a saturating dose of anti-IL-17 RA MAb and 90 mg/kg Compound 1.136 became evident after the second day of treatment (FIG. 6B (also, see FIG. 7B for direct comparison of anti-IL-17RA MAb treatment to the isotype-matched control for this MAb at 500 μg/mouse/day)).

We next examined sections of mouse ears taken after 4 daily treatments with PBS (control) or activated IL-36α for measurement of epidermal thickness (FIG. 8A, FIG. 8B, & FIG. 9). In agreement with the direct measurements of ear swelling shown in FIG. 6, epidermal thickening was evident in the IL-36α-treated ear versus the PBS-treated ear (FIG. 9A). Administration of Compound 1.136 or anti-IL-17RA significantly reduced IL-36α-mediated epidermal thickness (FIG. 9B).

Administration of Compound 1.136 reduced IL-36α-induced dermal, epidermal and overall skin thickness (FIG. 8C), In addition, the stratum corneum remained intact and leukocyte infiltration was reduced. Dosing with anti-IL-17RA had a beneficial effect on IL-36-treated skin as well (FIG. 8D).

We next assessed the effects of Compound 1.136 on the inflammatory cell subsets accumulating within IL-36 treated skin by flow cytometry (FIG. 10). Immune cells were isolated from the skin after 4 daily ear injections of IL-36α and treatment with Compound 1.136 or α-IL-17RA MAb. We found that Compound 1.136 significantly reduced the accumulation of CD4+ T cells, neutrophils and inflammatory iDCs. In contrast, α-IL-17RA did not reduce the accumulation of CD4+ T cells, but had effects similar to Compound 1.136 on neutrophils and iDCs.

Pustular psoriasis is a rare skin disorder comprising several subtypes, including both generalized and localized forms (Benjegerdes et al. *Psoriasis (Auckl)* 2016; 6:131-44. Mahil et al. *Semin Immunopathol* 2016; 38(1):11-27. Navarini et al. *J Eur Acad Dermatol Venereol* 2017; 31(11): 1792-9.). The generalized form (GPP) is associated with significant morbidity, and in some cases, mortality (Borges-Costa et al. *Am J Clin Dermatol* 2011; 12(4):271-6.). Loss-of-function mutations in the IL-36RN gene are common in GPP patients, especially those without concomitant symptoms of plaque psoriasis (Marrakchi et al. *N Engl J Med* 2011; 365(7):620-8.). The IL-36RN gene encodes a protein known as the IL-36 receptor antagonist (IL-36RA). In healthy individuals, IL-36RA competes with activated IL36α, β and/or γ cytokines for binding to the IL36 receptor (IL-36R), giving this protein anti-inflammatory properties that help maintain homeostasis. Aberrant structure and function of IL-36RA engenders dysregulated secretion of inflammatory cytokines and chemokines (Marrakchi et al. *N Engl J Med* 2011; 365(7):620-8.). Here we report that a small molecule antagonist of CCR6/CXCR2 was at more effective than anti-IL-17 therapy in reducing skin thickness and leukocyte infiltration after direct intradermal injection of activated IL-36α into mouse skin.

GPP is characterized by a widespread eruption of pustules and erythematous plaques. In the acute variant, patients usually appear systemically ill because the sudden eruption of pustules is accompanied by pain and fever. Life threatening leukocytosis, electrolyte abnormalities, hypoalbuminemia and elevated liver enzymes can also occur in the acute variant (Benjegerdes et al. *Psoriasis (Auckl)* 2016; 6:131-44). There are no approved treatments for GPP. Due to the rare occurrence of this disease, there is no standardized method of assessing the response to treatment. Data on treatment outcomes consist primarily of retrospective studies, case reports and expert opinion (Benjegerdes et al. *Psoriasis (Auckl)* 2016; 6:131-44. Robinson et al. *J Am Acad Dermatol* 2012; 67(2):279-88.).

Current treatments for GPP involve supportive care for those patients who are systemically ill, followed by medical treatments to control the skin disease (Robinson et al. *J Am Acad Dermatol* 2012, 67(2):279-88.). Chronic, slowly progressing disease is typically managed by oral retinoids or methotrexate. Acute disease is treated with cyclosporine or one of the anti-TNFα biologics. None of these treatments are highly effective, and all have side effects (Robinson et al. *J Am Acad Dermaiol* 2012; 67(2):279-88.). Thus, there is an unmet clinical need for new treatments and new clinical targets for GPP management.

In addition to the T cells and neutrophils that accumulate in IL-36 treated skin, this model also generates large numbers of myeloid cells we believe to be iDC. This latter population expresses markers of both DCs and macrophages. Since these cells do not express FLT3/CD135, we believe them to be derived from monocytes rather than classical DC. It has been previously demonstrated that monocyte-derived DC from human blood express high levels of IL-36R (Foster et al. *J Immunol* 2014; 192(12):6053-61.). If the iDC from mouse skin prove to have similar properties to human blood monocyte-derived DC, these cells may be important modulators of IL-36-induced inflammation in the model used in the present study.

We used the IL36α model to compare the effectiveness of Compound 1.136 to that of an α-IL-17RA MAb. Biologics against the IL-17 axis are often used as a second-line treatment for GPP in the clinic (Imafuku et al, *J Dermatol* 2016; 43(9):1011-7.). We found the 90 mg/kg dose of Compound 1.136 to be significantly more effective than α-IL-17RA (500 mg/mouse/day) at reducing ear swelling (FIG. 8). Although α-IL-17RA treatments significantly reduced the accumulation of neutrophils and iDC in skin, the $CD4^+$ αβ T cell count was not affected. Thus, the additional anti-inflammatory effect of Compound 1.136 over and above that of α-IL-17RA closely corresponds to the reduction in $CD4^+$ αβ T cells.

In summary, we have shown that the inflammation resulting from activated IL-36α skin injections involves neutrophil, iDC and CD4 T cell accumulation, similar to what is seen in GPP patients. Selective inhibition of CCR6 and CXCR2 by Compound 1.136 reduced all three of these inflammatory cell types and ameliorated skin inflammation. Blockade of the IL-17 axis reversed neutrophil and iDC but not CD4 T cell accumulation in skin. Compound 1.136 is a more effective therapeutic agent than the saturating concentrations of an α-IL-17RA monoclonal antibody assessed in this IL-36α induced model of psoriasis. These findings suggest that CCR6/CXCR2 antagonism may constitute a novel target class, and a mechanistically distinct therapeutic approach to treating dysregulation of the IL-36 cytokine axis (as in GPP), by specifically acting upon the inflammatory cells that likely mediate the disease.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating generalized pustular psoriasi (GPP) in a subject in need thereof, said method comprising administering to the subject an effective amount of a compound having the formula

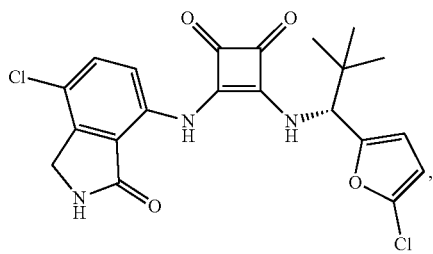

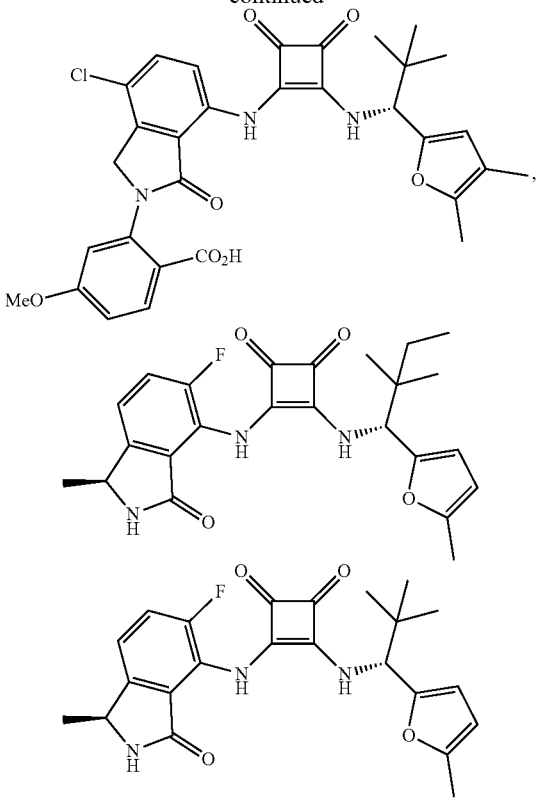

or a pharmaceutically acceptable salt thereof.

2. The method of claim 1, wherein said compound has the formula:

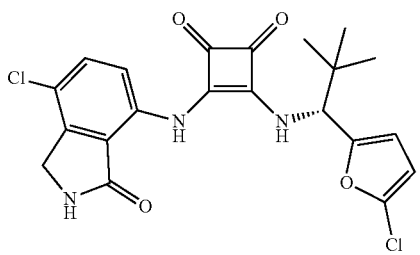 [SMILES: CC(C)(C)[C@@H](Nc1c(Nc2ccc(Cl)c3c2C(=O)NC3)c(=O)c1=O)c1ccc(Cl)o1]

or a pharmaceutically acceptable salt thereof.

3. The method of claim 1, wherein said compound has the formula:

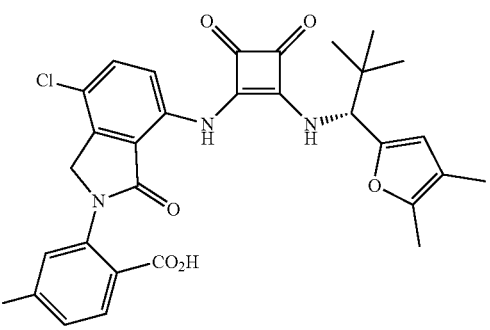

or a pharmaceutically acceptable salt thereof.

4. The method of claim 1, wherein said compound has the formula:
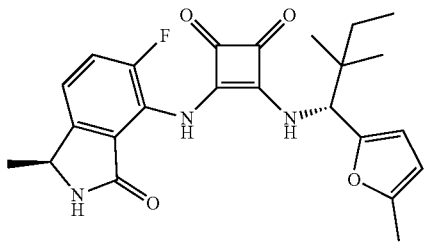 [SMILES: CCC(C)(C)[C@@H](Nc1c(Nc2c(F)ccc3c2C(=O)N[C@H]3C)c(=O)c1=O)c1ccc(C)o1]
or a pharmaceutically acceptable salt thereof.
5. The method of claim 1, wherein said compound has the formula:
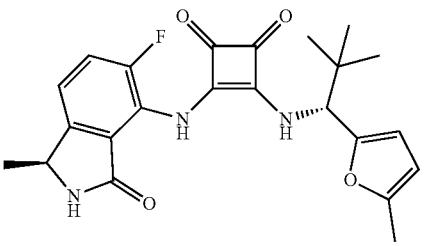 [SMILES: Cc1ccc([C@H](Nc2c(Nc3c(F)ccc4c3C(=O)N[C@H]4C)c(=O)c2=O)C(C)(C)C)o1]
or a pharmaceutically acceptable salt thereof.
6. The method of claim 1, wherein the subject is a human subject.
* * * * *